(12) United States Patent
Cance et al.

(10) Patent No.: US 8,003,613 B2
(45) Date of Patent: Aug. 23, 2011

(54) METHODS AND COMPOSITIONS FOR INDUCING APOPTOSIS

(75) Inventors: William G. Cance, Orchard Park, NY (US); Vita Golubovskaya, Orchard Park, NY (US); Elena V. Kurenova, West Falls, NY (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 1050 days.

(21) Appl. No.: 10/579,529

(22) PCT Filed: Nov. 17, 2004

(86) PCT No.: PCT/US2004/038363
§ 371 (c)(1),
(2), (4) Date: Mar. 6, 2007

(87) PCT Pub. No.: WO2005/049852
PCT Pub. Date: Jun. 2, 2005

(65) Prior Publication Data
US 2009/0123463 A1  May 14, 2009

Related U.S. Application Data

(60) Provisional application No. 60/523,232, filed on Nov. 17, 2003.

(51) Int. Cl.
| A61K 38/10 | (2006.01) |
| A61K 38/04 | (2006.01) |
| A61K 39/385 | (2006.01) |
| C07K 7/08 | (2006.01) |
| C07K 16/46 | (2006.01) |
| C07K 14/71 | (2006.01) |

(52) U.S. Cl. ...... 514/18.9; 514/1.1; 514/19.1; 514/19.2; 514/21.5; 514/21.6; 424/178.1; 424/182.1; 530/300; 530/327; 530/391.1; 530/391.7; 530/402

(58) Field of Classification Search ............... 530/300, 530/327, 402, 391.1, 391.7; 424/178.1, 182.1; 514/1.1, 18.9, 19.1, 21.5, 21.6
See application file for complete search history.

(56) References Cited

U.S. PATENT DOCUMENTS

| 6,100,071 A * | 8/2000 | Davis-Smyth et al. ...... 435/69.7 |
| 6,962,696 B1 * | 11/2005 | Bermudes et al. ........... 424/93.4 |
| 7,361,730 B1 * | 4/2008 | Sauk .............................. 530/300 |

FOREIGN PATENT DOCUMENTS

| WO | WO 00/21560 | 4/2000 |
| WO | WO 00/54805 | 9/2000 |

OTHER PUBLICATIONS

Hungerford, J.E. et al, The Journal of Cell Biology, 135(5): 1383-1390, 1996.*
Garces, C.A., et al. Cancer Res. 66(3): 1446-1454, 2006.*

* cited by examiner

*Primary Examiner* — Alana M Harris
*Assistant Examiner* — Anne Holleran
(74) *Attorney, Agent, or Firm* — Edwards Angell Palmer & Dodge LLP; Jeffrey D. Hsi; Elizabeth Spar

(57) ABSTRACT

The C-terminal domain of focal adhesion kinase (FAK-CD) was isolated using a Baculoviral system. Using phage display techniques, a phage encoding a 12 amino-acid peptide (peptide 35) and AV3 that binds to FAK-CD were identified. The peptides were also conjugated to TAT-FITC to produce a fluorescently labeled chimeric molecule capable of penetrating cell membranes. Contacting various breast cancer cell lines with these molecule caused detachment, rounding, apoptosis and cell death. These effects were not observed in normal (non-cancerous) breast cells.

14 Claims, 11 Drawing Sheets

Figure 1: Phage Display

Figure 2: Binding of Peptide-35 to purified FAK-CD *in vitro*, but not with control.

Figure 3: Peptide-35 causes displacement of FAK from focal adhesions in BT474, BT20, and MCF7 cells. This was not seen when scrambled Peptide-35 was used. Peptide-35 also causes rounding and detachment in BT474 cells, but not in normal MCF10A breast cells.

SEQUENCE LISTING

<160> NUMBER OF SEQ ID NOS: 5

<210> SEQ ID NO 1
<211> LENGTH: 12
<212> TYPE: PRT
<213> ORGANISM: Homo sapiens

<400> SEQUENCE: 1

Trp His Trp Gln Trp Thr Pro Trp Ser Ile Gln Pro
 1               5                  10

<210> SEQ ID NO 2
<211> LENGTH: 12
<212> TYPE: PRT
<213> ORGANISM: Homo sapiens

<400> SEQUENCE: 2

His Pro Trp Gln Trp Thr Ile Ser Trp Pro Gln Trp
 1               5                  10

<210> SEQ ID NO 3
<211> LENGTH: 12
<212> TYPE: PRT
<213> ORGANISM: Homo sapiens

<400> SEQUENCE: 3

Trp His Trp Arg Pro Trp Thr Pro Cys Lys Met Phe
 1               5                  10

<210> SEQ ID NO 4
<211> LENGTH: 12
<212> TYPE: PRT
<213> ORGANISM: Homo sapiens

<400> SEQUENCE: 4

Met Arg Trp Thr His Phe Trp Pro Cys Pro Trp Lys
 1               5                  10

<210> SEQ ID NO 5
<211> LENGTH: 11
<212> TYPE: PRT
<213> ORGANISM: Human immunodeficiency virus

<400> SEQUENCE: 5

Tyr Gly Arg Lys Lys Arg Arg Gln Arg Arg Arg
 1               5                  10

US 8,003,613 B2

METHODS AND COMPOSITIONS FOR INDUCING APOPTOSIS

CROSS-REFERENCE TO RELATED APPLICATIONS

This application is the national stage entry of International Application No. PCT/US2004/038363, filed Nov. 17, 2004, which claims priority to U.S. Provisional Application No. 60/523,232, filed Nov. 17, 2003, the disclosures of both of which are hereby incorporated by reference.

STATEMENT REGARDING FEDERALLY SPONSORED RESEARCH AND DEVELOPMENT

This invention was made with United States government support under grant CA65910 awarded by the National Institutes of Health. The United States Government has certain rights in the invention.

FIELD OF THE INVENTION

Compositions, peptides and methods for modulating cellular activity. In particular, the compositions are shown to induce apoptosis and inhibit cell motility, metastasis of tumor cells and cellular invasion.

BACKGROUND OF THE INVENTION

Focal adhesion kinase (FAK) is a 125 kDa non-receptor protein tyrosine kinase that is concentrated at focal adhesions, the contact sites between cells and the extracellular matrix (ECM). FAK is involved in integrin signaling, cellular motility, and survival and is expressed at high levels in breast, colon, thyroid cancers, and in sarcomas. Interruption of normal FAK function causes cancer cells to become non-adherent and to undergo apoptosis.

Despite progress in understanding the biology of FAK and its signaling complex, much remains unknown as to how FAK interacts with its signaling partners to resist activation of the apoptotic cascade. The carboxy-terminus of FAK contains the focal adhesion targeting (FAT) domain of the protein. The FAT domain is critical for recruitment of FAK to focal adhesions and contains binding sites for two focal adhesion-associated proteins, paxillin and talin. Agents that modulate binding of FAK or FAT to other cellular components would be of use in further understanding the role of FAK in apoptosis, and may also be useful for killing cancer cells.

SUMMARY

The invention relates to the discovery of a 12-amino acid peptide (peptide 35, WHWQWTPWSIQP (SEQ ID NO:1); and AV3, WHWRPWTPCKMF (SEQ ID NO: 3)) that causes displacement of C-terminal part of FAK from focal adhesions and induces detachment and apoptosis in different cancer cell lines. The apoptotic effect was not observed in normal breast cancer cell line MCF10A nor when a control peptide was used (scrambled peptide 35; HPWQWTISWPQW; SEQ ID NO:2). Thus, Peptide 35 (SEQ ID NO: 1) and AV3 (SEQ ID NO: 3) can be used to target FAK and induce apoptosis in human cancer cell lines.

Accordingly, the invention features an agent that specifically binds focal adhesion kinase and induces apoptosis in a cell that expresses focal adhesion kinase. The agent can include the amino acid sequence of SEQ ID NO: 1 and/or SEQ ID NO: 3 or a variant thereof, and optionally a membrane permeabilization domain, for example, a TAT peptide such as identified by SEQ ID NO: 5.

In another embodiment, the invention features a method for inducing apoptosis in a cancer cell. This method includes the step of contacting the cancer cell with a composition that specifically binds focal adhesion kinase at a site that is specifically bound by a peptide comprising amino acid sequence SEQ ID NO:1 and/or SEQ ID NO: 3. The composition can include the amino acid sequence of SEQ ID NO:1 and/or SEQ ID NO: 3 or a variant thereof.

In another preferred embodiment, the functional role of FAK-VEGFR-3 interaction in apoptosis, motility and invasion is determined for identification of compositions that modulate such activities. For example, identification of compositions comprising candidate agents (e.g. nucleic acids, peptides and the like) that specifically bind focal adhesion kinase and induces apoptosis in a cell that expresses focal adhesion kinase.

In another preferred embodiment, a peptide used for treating a disorder such as cancer, is about 50% homologous to the peptide as identified by SEQ ID NO: 1; more preferably, a peptide used for treating a disorder such as cancer, is about 60% homologous to the peptide as identified by SEQ ID NO: 1; more preferably, a peptide used for treating a disorder such as cancer, is about 70% homologous to the peptide as identified by SEQ ID NO: 1; more preferably, a peptide used for treating a disorder such as cancer, is about 80% homologous to the peptide as identified by SEQ ID NO: 1; more preferably, a peptide used for treating a disorder such as cancer, is about 90% homologous to the peptide as identified by SEQ ED NO: 1; more preferably, a peptide used for treating a disorder such as cancer, is about 95%, 96%, 97%, 98%, 99% and 99.9% homologous to the peptide as identified by SEQ ID NO: 1.

In another preferred embodiment, a nucleic acid molecule encoding a peptide used for treating a disorder such as cancer, encodes a peptide that is about 50% homologous to the peptide as identified by SEQ ID NO: 1; more preferably, a nucleic acid molecule encoding a peptide used for treating a disorder such as cancer, encodes a peptide that is about 60% homologous to the peptide as identified by SEQ ID NO: 1; more preferably, a nucleic acid molecule encoding a peptide used for treating a disorder such as cancer, encodes a peptide that is about 70% homologous to the peptide as identified by SEQ ID NO: 1; more preferably, a nucleic acid molecule encoding a peptide used for treating a disorder such as cancer, encodes a peptide that is about 80% homologous to the peptide as identified by SEQ ID NO: 1; more preferably, a nucleic acid molecule encoding a peptide used for treating a disorder such as cancer, encodes a peptide that is about 90% homologous to the peptide as identified by SEQ ID NO: 1; more preferably, a nucleic acid molecule encoding a peptide used for treating a disorder such as cancer, encodes a peptide that is about 95%, 96%, 97%, 98%, 99% and 99.9% homologous to the peptide as identified by SEQ ID NO: 1.

In another preferred embodiment, a peptide used for treating a disorder such as cancer, is about 50% homologous to the peptide as identified by SEQ ID NO: 3; more preferably, a peptide used for treating a disorder such as cancer, is about 60% homologous to the peptide as identified by SEQ ID NO: 3; more preferably, a peptide used for treating a disorder such as cancer, is about 70% homologous to the peptide as identified by SEQ ID NO: 3; more preferably, a peptide used for treating a disorder such as cancer, is about 80% homologous to the peptide as identified by SEQ ID NO: 3; more preferably, a peptide used for treating a disorder such as cancer, is about 90% homologous to the peptide as identified by SEQ ID NO: 3; more preferably, a peptide used for treating a disorder such as cancer, is about 95%, 96%, 97%, 98%, 99% and 99.9% homologous to the peptide as identified by SEQ ID NO: 3.

In another preferred embodiment, a nucleic acid molecule encoding a peptide used for treating a disorder such as cancer, encodes a peptide that is about 50% homologous to the peptide as identified by SEQ ID NO: 3; more preferably, a nucleic acid molecule encoding a peptide used for treating a disorder such as cancer, encodes a peptide that is about 60% homologous to the peptide as identified by SEQ ID NO: 3; more preferably, a nucleic acid molecule encoding a peptide used for treating a disorder such as cancer, encodes a peptide that is about 70% homologous to the peptide as identified by SEQ ID NO: 3; more preferably, a nucleic acid molecule encoding a peptide used for treating a disorder such as cancer, encodes a peptide that is about 80% homologous to the peptide as identified by SEQ ID NO: 3; more preferably, a nucleic acid molecule encoding a peptide used for treating a disorder such as cancer, encodes a peptide that is about 90% homologous to the peptide as identified by SEQ ID NO: 3; more preferably, a nucleic acid molecule encoding a peptide used for treating a disorder such as cancer, encodes a peptide that is about 95%, 96%, 97%, 98%, 99% and 99.9% homologous to the peptide as identified by SEQ ID NO: 3.

In another preferred embodiment, the composition comprises a chimeric molecule comprising the amino acid sequence of SEQ ID NO: 1 and/or SEQ ID NO: 3 or variants thereof, and a membrane permeabilization domain.

In another preferred embodiment, a method for inducing apoptosis in a cancer cell comprises contacting the cancer cell with a composition that specifically binds focal adhesion kinase at a site that is specifically bound by a peptide comprising the amino acid sequence of SEQ ID NO:1 and/or SEQ ID NO: 3 or variants thereof.

In another preferred embodiment, the invention provides a pharmaceutical composition comprising a chimeric fusion molecule, wherein the chimeric fusion molecule comprises an antigen binding domain and a therapeutic effector domain. Preferably, the pharmaceutical composition is used in treating cancer.

In another preferred embodiment, the antigen binding domain comprises an isolated antibody or fragments thereof. The isolated antibody or fragments thereof comprises immunoglobulin heavy and light chains and/or immunoglobulin variable and constant regions. Preferably, the isolated immunoglobulin variable region comprise Fab, Fab', F(ab')$_2$, and Fv fragments and/or immunoglobulin constant regions, $C_H1$, hinge, $C_H2$ and $C_H3$.

In another preferred embodiment, the isolated antibody or fragments thereof are fused to a therapeutic effector domain, for example SEQ ID NO: 1 and/or SEQ ID NO: 3 or variants thereof. In accordance with the invention, the isolated antibody is fused to the therapeutic effector domain via the immunoglobulin constant regions, $C_H1$, hinge, $C_H2$ or $C_H3$. Preferably, the isolated antibody is fused to the therapeutic effector domain via the immunoglobulin constant region, $C_H3$.

In another preferred embodiment, the invention provides for an isolated nucleic acid molecule encoding the chimeric molecule as described infra and nucleic acid molecules encoding the chimeric molecule.

In another preferred embodiment, the chimeric fusion protein is administered to a patient in need of such therapy and modulates the activity of the tumor.

In another preferred embodiment, the invention provides a method for targeting SEQ ID NO: 1 and/or SEQ ID NO: 3 to a tumor cell in an animal subject, the method comprising the step of administering to the animal subject a composition comprising a chimeric molecule comprising a domain that modulates apoptosis, cell motility and/or metastasis, cell permeability domain and/or an Ig domain.

In another preferred embodiment, the invention provides a method for treating a tumor in an animal subject, the method comprising the step of administering to the animal subject a composition comprising a chimeric fusion molecule composition, as described above. Preferably, the chimeric fusion molecule composition is administered with one or more therapeutic agents and/or adjuvants.

In other preferred embodiments, the therapeutic agents comprise antiangiogenic antibodies, tumor antigen specific antibodies, glycolysis inhibitor agents, anti-angiogenic agents, chemotherapeutic agents, radiotherapy, radionuclides, or drugs that ameliorate the symptoms of a patient.

In accordance with the invention, the composition that specifically binds focal adhesion kinase and induces apoptosis in a cell that expresses focal adhesion kinase or a chimeric fusion molecule composition is administered to a patient in combination with metronomic therapy. For example, administration of continuous low-doses of the chimeric fusion molecule and one or more therapeutic agents. Therapeutic agents can include, for example, chemotherapeutic agents such as, cyclophosphamide (CTX, 25 mg/kg/day, p.o.), taxanes (paclitaxel or docetaxel), busulfan, cisplatin, cyclophosphamide, methotrexate, daunorubicin, doxorubicin, melphalan, cladribine, vincristine, vinblastine, and chlorambucil.

In another preferred embodiment, the invention provides a kit comprising a composition that specifically binds focal adhesion kinase and induces apoptosis in a cell that expresses focal adhesion kinase or a chimeric fusion molecule composition. The composition can include the amino acid sequence of SEQ ID NO:1 and/or SEQ ID NO: 3 or a variant thereof, and optionally a membrane permeabilization domain, for example, a TAT peptide such as identified by SEQ ID NO: 5.

In accordance with the invention the antibody or fragments thereof is preferably, polyclonal or monoclonal. Further provided is a pharmaceutical composition for administering the chimeric molecule to a patient in need thereof. The compositions may be lyophilized and reagents and/or pharmaceutical compositions for reconstituting and administering the lyophilized compositions are provided.

Additionally, instructions for carrying out the method for administering the molecules to a patient, are provided.

Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions will control. In addition, the particular embodiments discussed below are illustrative only and not intended to be limiting.

Other aspects of the invention are described infra.

BRIEF DESCRIPTION OF THE DRAWINGS

The invention is pointed out with particularity in the appended claims. The above and further advantages of this invention may be better understood by referring to the following description taken in conjunction with the accompanying drawings, in which:

DETAILED DESCRIPTION

Figure 1:
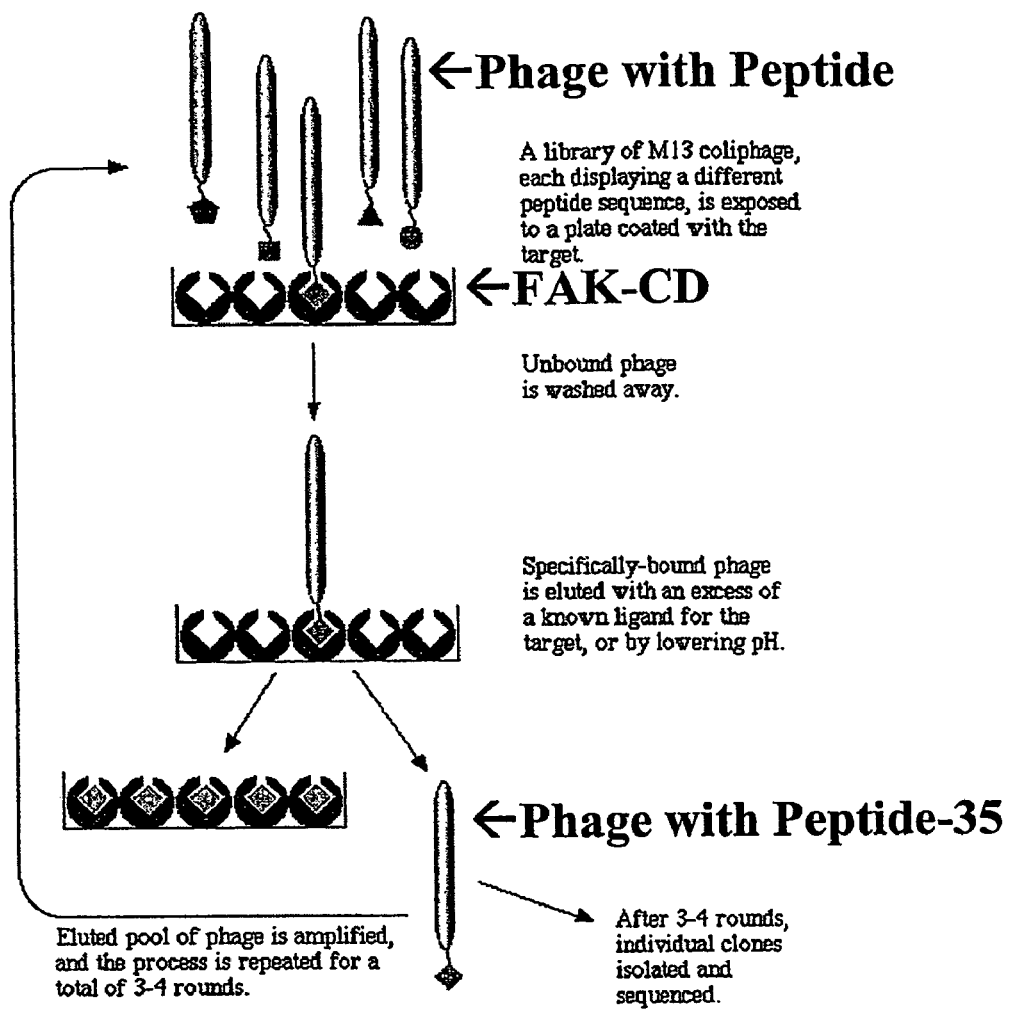
FIG. 1 is a highly schematic overview of phage display methods used to isolate peptide-35.

This invention encompasses compositions and methods relating to the use of Peptide 35 (SEQ ID NO: 1) and/or AV3 (SEQ ID NO: 3) and variants thereof to induce apoptosis in cancer cells. The below described preferred embodiments illustrate adaptations of these compositions and methods. Nonetheless, from the description of these embodiments, other aspects of the invention can be made and/or practiced based on the description provided below.

Prior to setting forth the invention, definitions of certain terms which are used in this disclosure are set forth below:

DEFINITIONS

Unless otherwise defined, all technical terms used herein have the same meaning as commonly understood by one of ordinary skill in the art to which this invention belongs. Commonly understood definitions of molecular biology terms can be found in Rieger et al., Glossary of Genetics: Classical and Molecular, 5th edition, Springer-Verlag: New York, 1991; and Lewin, Genes V, Oxford University Press: New York, 1994.

As used herein, the terms "peptide," "protein," and "polypeptide" are used synonymously to mean any peptide-linked chain of amino acids, regardless of length or post-translational modification, e.g., glycosylation or phosphorylation. A "purified" polypeptide is one that has been substantially separated or isolated away from other polypeptides in a cell, organism, or mixture in which the polypeptide occurs (e.g., 30, 40, 50, 60, 70, 80, 90, 95, 96, 97, 98, 99, 100% free of contaminants).

As used herein, the phrase "native peptide 35" means a polypeptide corresponding to the amino acid sequence shown herein as SEQ ID NO: 1. The same terminology applies to AV3 (SEQ ID NO: 3).

The phrase "peptide 35 mutant" or a "mutant peptide 35 molecule" means an peptide 35 (SEQ ID NO: 1) in which one or more of the amino acids differ from the corresponding amino acids in the native peptide 35.

A "mutation" in a polypeptide refers to the substitution of an amino acid at a particular position in a polypeptide with a different amino acid at that position. In some cases, a mutation can be the deletion, addition, or substitution of more than one amino acid in a polypeptide. The mutation does not require an actual removal and substitution of the amino acid(s) in question. The protein can be created de novo with the replacement amino acid in the position(s) of the desired mutation(s) so the net result is equivalent to the replacement of the amino acid in question.

As used herein, "sequence identity" means the percentage of identical subunits at corresponding positions in two sequences when the two sequences are aligned to maximize subunit matching, i.e., taking into account gaps and insertions. When a subunit position in both of the two sequences is occupied by the same monomeric subunit, e.g., if a given position is occupied by an alanine in each of two polypeptide molecules, then the molecules are identical at that position. For example, if 7 positions in a sequence 10 amino acids in length are identical to the corresponding positions in a second 10 amino acid sequence, then the two sequences have 70% sequence identity. Sequence identity is typically measured using sequence analysis software (e.g., Sequence Analysis Software Package of the Genetics Computer Group, University of Wisconsin Biotechnology Center, 1710 University Avenue, Madison, Wis. 53705).

The term "specifically binds", as used herein, when referring to a polypeptide or receptor, refers to a binding reaction which is determinative of the presence of the protein or polypeptide or receptor in a heterogeneous population of proteins and other biologics. Generally, a first molecule that "specifically binds" a second molecule has a binding affinity greater than about $10^5$ (e.g., $10^6$, $10^7$, $10^8$, $10^9$, $10^{10}$, $10^{11}$, and $10^{12}$ or more) moles/liter for that second molecule.

As used herein, the singular forms "a", "an" and "the" include plural referents unless the context clearly dictates otherwise.

As used herein, "antibody" refers to single chain, two-chain, and multi-chain proteins and glycoproteins belonging to the classes of polyclonal, monoclonal, chimeric, and hetero immunoglobulins (monoclonal antibodies being preferred); it also includes synthetic and genetically engineered variants of these immunoglobulins. "Antibody fragment" includes Fab, Fab', F(ab')$_2$, and Fv fragments, as well as any portion of an antibody having specificity toward a desired target epitope or epitopes.

As used herein, the term "immunoglobulin" refers to a protein consisting of one or more polypeptides substantially encoded by immunoglobulin genes. The recognized immunoglobulin genes include the κ, λ, α, γ (IgG1, IgG2, IgG3, IgG4), δ, ε and μ constant region genes, as well as the myriad immunoglobulin variable region genes. Full-length immunoglobulin "light chains" (about 25 KDa or 214 amino acids) are encoded by a variable region gene at the NH$_2$-terminus (about 110 amino acids) and a kappa or lambda constant region gene at the COOH-terminus. Full-length immunoglobulin "heavy chains" (about 50 KDa or 446 amino acids), are similarly encoded by a variable region gene (about 116 amino acids) and one of the other aforementioned constant region genes, e.g., gamma (encoding about 330 amino acids). One form of immunoglobulin constitutes the basic structural unit of an antibody. This form is a tetramer and consists of two identical pairs of immunoglobulin chains, each pair having one light and one heavy chain. In each pair, the light and heavy chain variable regions are together responsible for binding to an antigen, and the constant regions are responsible for the antibody effector functions. In addition to antibodies, immunoglobulins may exist in a variety of other forms including, for example, Fv, Fab, and F(ab')$_2$, as well as bifunctional hybrid antibodies (e.g., Lanzavecchia et al., *Eur. J. Immunol.* 17, 105 (1987)) and in single chains (e.g., Huston et al., *Proc. Natl. Acad. Sci. U.S.A.,* 85, 5879-5883 (1988) and Bird et al., *Science,* 242, 423-426 (1988), which are incorporated herein by reference). (See, generally, Hood et al., "Immunology", Benjamin, N.Y., 2nd ed. (1984), and Hunkapiller and Hood, Nature, 323, 15-16 (1986), which are incorporated herein by reference).

An immunoglobulin light or heavy chain variable region consists of a "framework" region interrupted by three hypervariable regions, also called CDR's. The extent of the framework region and CDR's have been precisely defined (see, "Sequences of Proteins of Immunological Interest," E. Kabat et al., U.S. Department of Health and Human Services, (1983); which is incorporated herein by reference). The sequences of the framework regions of different light or heavy chains are relatively conserved within a species. As used herein, a "human framework region" is a framework region that is substantially identical (about 85% or more, usually 90-95% or more) to the framework region of a naturally occurring human immunoglobulin. The framework region of an antibody, that is the combined framework regions of the constituent light and heavy chains, serves to position and align the CDR's. The CDR's are primarily responsible for binding to an epitope of an antigen.

As used herein, "humanized antibody" refers to an antibody derived from a non-human antibody, typically murine, that retains or substantially retains the antigen-binding properties of the parent antibody but which is less immunogenic in humans. This may be achieved by various methods including (a) grafting only the non-human CDRs onto human framework and constant regions with or without retention of critical framework residues, or (b) transplanting the entire non-human variable domains, but "cloaking" them with a human-like section by replacement of surface residues. Such methods as are useful in practicing the present invention include those disclosed in Jones et al., Morrison et al., *Proc. Nat'l Acad. Sci. USA,* 81:6851-6855 (1984); Morrison and Oi, *Adv. Immunol.,* 44:65-92 (1988); Verhoeyen et al., *Science,* 239: 1534-1536 (1988); Padlan, *Mol. Immunol.,* 28:489-498 (1991); Padlan, *Mol. Immunol.,* 31(3):169-217 (1994).

As used herein, "Complementarity Determining Region" (CDR) refers to amino acid sequences which together define the binding affinity and specificity of the natural Fv region of a native immunoglobulin binding site as delineated by Kabat et al. (1991).

As used herein, "Framework Region" (FR) refers to amino acid sequences interposed between CDRs. These portions of the antibody serve to hold the CDRs in an appropriate orientation for antigen binding. In the antibodies and antibody fragments of the present invention, comprise their fully human native amino acid sequences and/or comprise amino acid sequence modifications necessary to retain or increase binding affinity and/or binding specificity.

As used herein, "constant region" refers to the portion of the antibody molecule which confers effector functions. Preferred constant regions are gamma 1 (IgG1), gamma 3 (IgG3) and gamma 4 (IgG4). More preferred is a constant region of the gamma 3 (IgG3) isotype. The light chain constant region can be of the kappa or lambda type, preferably of the kappa type.

Substantially homologous immunoglobulin sequences are those which exhibit at least about 85% homology, usually at least about 90%, and preferably at least about 95% homology with a reference immunoglobulin protein.

As used herein, "therapeutic effector domain" refers to any molecule that modulates a cellular activity or is cytolytic. For example, a cytokine such as IL-2 modulates T-cell activity; endostatin modulates cellular activity by down-regulating VEGF expression in tumor cells. A modulatory polypeptide or a cytolytic polypeptide is fused to at least one of the first or second polypeptides or the peptide linker. It is preferred that the modulatory polypeptide binds focal adhesion kinase and induces apoptosis in a cell that expresses focal adhesion kinase. The agent can include the amino acid sequence of SEQ ID NO:1 and/or SEQ ID NO: 3 or a variant thereof, and optionally a membrane permeabilization domain, for example, a TAT peptide such as identified by SEQ ID NO: 5. However, the invention is not limited to SEQ ID NO: 1 and/or SEQ ID NO: 3. Other examples include, but not limited to, chemokines, angioarrestin, angiostatin (plasminogen fragment), anti-angiogenic antithrombin III, cartilage-derived inhibitor (CDI), CD59 complement fragment, fibronectin fragment, gro-beta, heparinases, heparin hexasaccharide fragment, human chorionic gonadotropin (hCG), interferon alpha/beta/gamma, interferon inducible protein (IP-10), interleukin-12, kringle 5 (plasminogen fragment), metalloproteinase inhibitors (TIMPs), 2-methoxyestradiol, placental ribonuclease inhibitor, plasminogen activator inhibitor, platelet factor-4 (PF4), prolactin 16 kD fragment, proliferin-related protein (PRP), various retinoids, tetrahydrocortisol-S, thrombospondin-1 (TSP-1), transforming growth factor-beta (TGF-β), vasculostatin, vasostatin (calreticulin fragment).

The term "polyclonal" refers to antibodies that are heterogeneous populations of antibody molecules derived from the sera of animals immunized with an antigen or an antigenic functional derivative thereof. For the production of polyclonal antibodies, various host animals may be immunized by injection with the antigen. Various adjuvants may be used to increase the immunological response, depending on the host species.

"Monoclonal antibodies" are substantially homogenous populations of antibodies to a particular antigen. They may be obtained by any technique which provides for the production of antibody molecules by continuous cell lines in culture. Monoclonal antibodies may be obtained by methods known to those skilled in the art. See, for example, Kohler, et al., *Nature* 256:495-497, 1975, and U.S. Pat. No. 4,376,110.

As used herein, a "pharmaceutically acceptable" component is one that is suitable for use with humans and/or animals without undue adverse side effects (such as toxicity, irritation, and allergic response) commensurate with a reasonable benefit/risk ratio.

As used herein, the term "safe and effective amount" or "therapeutic amount" refers to the quantity of a component which is sufficient to yield a desired therapeutic response without undue adverse side effects (such as toxicity, irritation, or allergic response) commensurate with a reasonable benefit/risk ratio when used in the manner of this invention. By "therapeutically effective amount" is meant an amount of a compound of the present invention effective to yield the desired therapeutic response. For example, an amount effective to delay the growth of or to cause a cancer, either a sarcoma or lymphoma, or to shrink the cancer or prevent metastasis. The specific safe and effective amount or therapeutically effective amount will vary with such factors as the particular condition being treated, the physical condition of the patient, the type of mammal or animal being treated, the duration of the treatment, the nature of concurrent therapy (if any), and the specific formulations employed and the structure of the compounds or its derivatives.

By "therapeutically effective amount" is meant an amount of a pharmaceutical composition having a therapeutically relevant effect. A therapeutically relevant effect relieves to some extent one or more symptoms of the disease or condition in the patient; or returns to normal either partially or completely one or more physiological or biochemical parameters associated with or causative of the disease or condition. Generally, a therapeutically effective amount is between about 1 mmole and 1 µmole of the molecule, depending on its $EC_{50}$ or $IC_{50}$ and on the age and size of the patient, and the disease associated with the patient.

As used herein, a "pharmaceutical salt" include, but are not limited to, mineral or organic acid salts of basic residues such as amines; alkali or organic salts of acidic residues such as carboxylic acids. Preferably the salts are made using an organic or inorganic acid. These preferred acid salts are chlorides, bromides, sulfates, nitrates, phosphates, sulfonates, formates, tartrates, maleates, malates, citrates, benzoates, salicylates, ascorbates, and the like. The most preferred salt is the hydrochloride salt.

As used herein, "cancer" refers to all types of cancer or neoplasm or malignant tumors found in mammals, including, but not limited to: leukemias, lymphomas, melanomas, carcinomas and sarcomas. Examples of cancers are cancer of the brain, breast, pancreas, cervix, colon, head and neck, kidney, lung, non-small cell lung, melanoma, mesothelioma, ovary, sarcoma, stomach, uterus and Medulloblastoma.

Additional cancers which can be treated the chimeric fusion molecule according to the invention include, for example, Hodgkin's Disease, Non-Hodgkin's Lymphoma, multiple myeloma, neuroblastoma, breast cancer, ovarian cancer, lung cancer, rhabdomyosarcoma, primary thrombocytosis, primary macroglobulinemia, small-cell lung tumors, primary brain tumors, stomach cancer, colon cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, cervical cancer, endometrial cancer, adrenal cortical cancer, and prostate cancer.

"Diagnostic" or "diagnosed" means identifying the presence or nature of a pathologic condition. Diagnostic methods differ in their sensitivity and specificity. The "sensitivity" of a diagnostic assay is the percentage of diseased individuals who test positive (percent of "true positives"). Diseased individuals not detected by the assay are "false negatives." Subjects who are not diseased and who test negative in the assay, are termed "true negatives." The "specificity" of a diagnostic assay is 1 minus the false positive rate, where the "false positive" rate is defined as the proportion of those without the disease who test positive. While a particular diagnostic method may not provide a definitive diagnosis of a condition, it suffices if the method provides a positive indication that aids in diagnosis.

The terms "patient" or "individual" are used interchangeably herein, and refers to a mammalian subject to be treated, with human patients being preferred. In some cases, the methods of the invention find use in experimental animals, in veterinary application, and in the development of animal models for disease, including, but not limited to, rodents including mice, rats, and hamsters; and primates.

"Sample" is used herein in its broadest sense. A sample comprising polynucleotides, polypeptides, peptides, antibodies and the like may comprise a bodily fluid; a soluble fraction of a cell preparation, or media in which cells were grown; a chromosome, an organelle, or membrane isolated or extracted from a cell; genomic DNA, RNA, or cDNA, polypeptides, or peptides in solution or bound to a substrate; a cell; a tissue; a tissue print; a fingerprint, skin or hair; and the like.

"Treatment" is an intervention performed with the intention of preventing the development or altering the pathology or symptoms of a disorder. Accordingly, "treatment" refers to both therapeutic treatment and prophylactic or preventative measures. Those in need of treatment include those already with the disorder as well as those in which the disorder is to be prevented. In tumor (e.g., cancer) treatment, a therapeutic agent may directly decrease the pathology of tumor cells, or render the tumor cells more susceptible to treatment by other therapeutic agents, e.g., radiation and/or chemotherapy. As used herein, "ameliorated" or "treatment" refers to a symptom which is approaches a normalized value (for example a value obtained in a healthy patient or individual), e.g., is less than 50% different from a normalized value, preferably is less than about 25% different from a normalized value, more preferably, is less than 10% different from a normalized value, and still more preferably, is not significantly different from a normalized value as determined using routine statistical tests.

The "treatment of cancer or tumor cells", refers to an amount of peptide molecule, described throughout the specification and in the Examples which follow, capable of invoking one or more of the following effects: (1) inhibition of tumor growth, including, (i) slowing down (ii) inhibiting angiogenesis and (ii) complete growth arrest; (2) reduction in the number of tumor cells; (3) maintaining tumor size; (4) reduction in tumor size; (5) inhibition, including (i) reduction, (ii) slowing down or (iii) complete prevention, of tumor cell infiltration into peripheral organs; (6) inhibition, including (i) reduction, (ii) slowing down or (iii) complete prevention, of metastasis; (7) enhancement of anti-tumor immune response, which may result in (i) maintaining tumor size, (ii) reducing tumor size, (iii) slowing the growth of a tumor, (iv) reducing, slowing or preventing invasion and/or (8) relief, to some extent, of the severity or number of one or more symptoms associated with the disorder.

As used herein, "an ameliorated symptom" or "treated symptom" refers to a symptom which approaches a normalized value, e.g., is less than 50% different from a normalized value, preferably is less than about 25% different from a normalized value, more preferably, is less than 10% different from a normalized value, and still more preferably, is not significantly different from a normalized value as determined using routine statistical tests.

As used herein, "metronomic" therapy refers to the administration of continuous low-doses of a therapeutic agent and/or chimeric fusion molecule described herein.

By the term "modulate," it is meant that any of the mentioned activities, are, e.g., increased, enhanced, increased, augmented, agonized (acts as an agonist), promoted, decreased, reduced, suppressed blocked, or antagonized (acts as an antagonist). Modulation can increase activity more than 1-fold, 2-fold, 3-fold, 5-fold, 10-fold, 100-fold, etc., over baseline values. Modulation can also decrease its activity below baseline values.

"Immunoassay" is an assay that uses an antibody to specifically bind an antigen (e.g., a marker). The immunoassay is characterized by the use of specific binding properties of a particular antibody to isolate, target, and/or quantity the antigen.

The term "DNA construct" and "vector" are used herein to mean a purified or isolated polynucleotide that has been artificially designed and which comprises at least two nucleotide sequences that are not found as contiguous nucleotide sequences in their natural environment.

As used herein, the term "administering a molecule to a cell" (e.g., an expression vector, nucleic acid, a angiogenic factor, a delivery vehicle, agent, and the like) refers to transducing, transfecting, microinjecting, electroporating, or shooting, the cell with the molecule. In some aspects, molecules are introduced into a target cell by contacting the target cell with a delivery cell (e.g., by cell fusion or by lysing the delivery cell when it is in proximity to the target cell).

A cell has been "transformed", "transduced", or "transfected" by exogenous or heterologous nucleic acids when such nucleic acids have been introduced inside the cell. Transforming DNA may or may not be integrated (covalently linked) with chromosomal DNA making up the genome of the cell. In prokaryotes, yeast, and mammalian cells for example, the transforming DNA may be maintained on an episomal element, such as a plasmid. In a eukaryotic cell, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations (e.g., at least about 10).

As used interchangeably herein, the terms "oligonucleotides", "polynucleotides", and "nucleic acids" include RNA, DNA, or RNA/DNA hybrid sequences of more than one nucleotide in either single chain or duplex form. The term "nucleotide" as used herein as an adjective to describe molecules comprising RNA, DNA, or RNA/DNA hybrid sequences of any length in single-stranded or duplex form. The term "nucleotide" is also used herein as a noun to refer to individual nucleotides or varieties of nucleotides, meaning a molecule, or individual unit in a larger nucleic acid molecule, comprising a purine or pyrimidine, a ribose or deoxyribose sugar moiety, and a phosphate group, or phosphodiester linkage in the case of nucleotides within an oligonucleotide or polynucleotide. Although the term "nucleotide" is also used herein to encompass "modified nucleotides" which comprise at least one modifications (a) an alternative linking group, (b) an analogous form of purine, (c) an analogous form of pyrimidine, or (d) an analogous sugar, all as described herein.

As used herein, "molecule" is used generically to encompass any vector, antibody, protein, drug and the like which are used in therapy and can be detected in a patient by the methods of the invention. For example, multiple different types of nucleic acid delivery vectors encoding different types of genes which may act together to promote a therapeutic effect, or to increase the efficacy or selectivity of gene transfer and/or gene expression in a cell. The nucleic acid delivery vector may be provided as naked nucleic acids or in a delivery vehicle associated with one or more molecules for facilitating entry of a nucleic acid into a cell. Suitable delivery vehicles include, but are not limited to: liposomal formulations, polypeptides; polysaccharides; lipopolysaccharides, viral formulations (e.g., including viruses, viral particles, artificial viral envelopes and the like), cell delivery vehicles, and the like.

As used herein, the term "oligonucleotide" refers to a polynucleotide formed from naturally occurring bases and pentofuranosyl groups joined by native phosphodiester bonds. This term effectively refers to naturally occurring species or synthetic species formed from naturally occurring subunits or their close homologs. The term "oligonucleotide" may also refer to moieties which function similarly to naturally occurring oligonucleotides but which have non-naturally occurring portions. Thus, oligonucleotides may have altered sugar moieties or intersugar linkages. Exemplary among these are the phosphorothioate and other sulfur-containing species which are known for use in the art. In accordance with some preferred embodiments, at least some of the phosphodiester bonds of the oligonucleotide have been substituted with a structure which functions to enhance the ability of the compositions to penetrate into the region of cells where the RNA or DNA whose activity to be modulated is located. It is preferred that such substitutions comprise phosphorothioate bonds, methyl phosphonate bonds, or short chain alkyl or cycloalkyl structures. In accordance with other preferred embodiments, the phosphodiester bonds are substituted with other structures which are, at once, substantially non-ionic and non-chiral, or with structures which are chiral and enantiomerically specific. Persons of ordinary skill in the art will be able to select other linkages for use in practice of the invention.

Oligonucleotides may also include species which include at least some modified base forms. Thus, purines and pyrimidines other than those normally found in nature may be so employed. Similarly, modifications on the pentofuranosyl portion of the nucleotide subunits may also be effected, as long as the essential tenets of this invention are adhered to. Examples of such modifications are 2'-O-alkyl- and 2'-halogen-substituted nucleotides. Some specific examples of modifications at the 2' position of sugar moieties which are useful in the present invention are OH, SH, $SCH_3$, F, $OCH_3$, OCN, $O(CH_2)_nNH_2$ or $O(CH_2)_nCH_3$ where n is from 1 to about 10, and other substituents having similar properties.

Biological Methods

Methods involving conventional molecular biology techniques are described herein. Such techniques are generally known in the art and are described in detail in methodology treatises such as Molecular Cloning: A Laboratory Manual, 2nd ed., vol. 1-3, ed. Sambrook et al., Cold Spring Harbor Laboratory Press, Cold Spring Harbor, N.Y., 1989; and Current Protocols in Molecular Biology, ed. Ausubel et al., Greene Publishing and Wiley-Interscience, New York, 1992 (with periodic updates).

Molecules that Bind FAK

Figure 2:
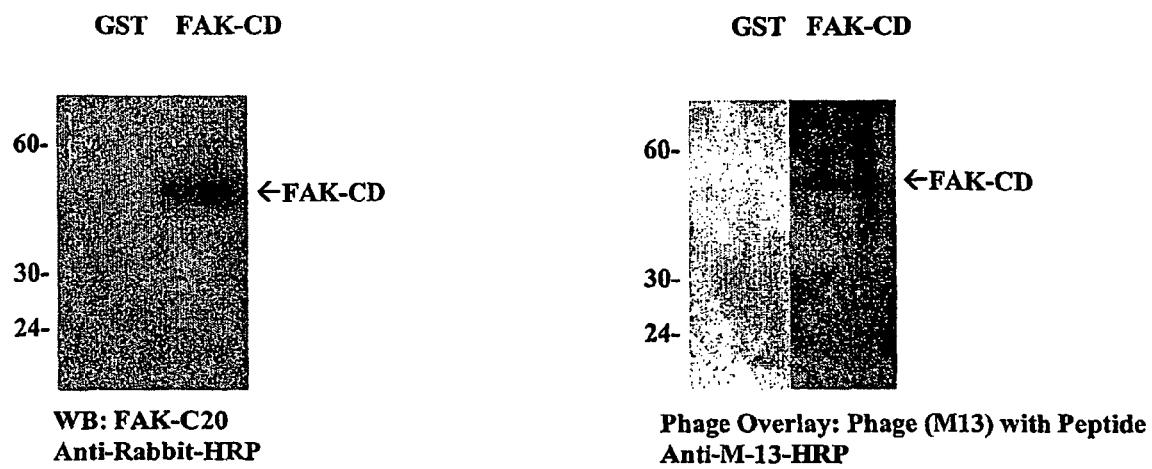
FIG. 2 is two Western blots/phage overlays showing that peptide-35 binds to specific sequences of FAK-CD.
Figure 3:
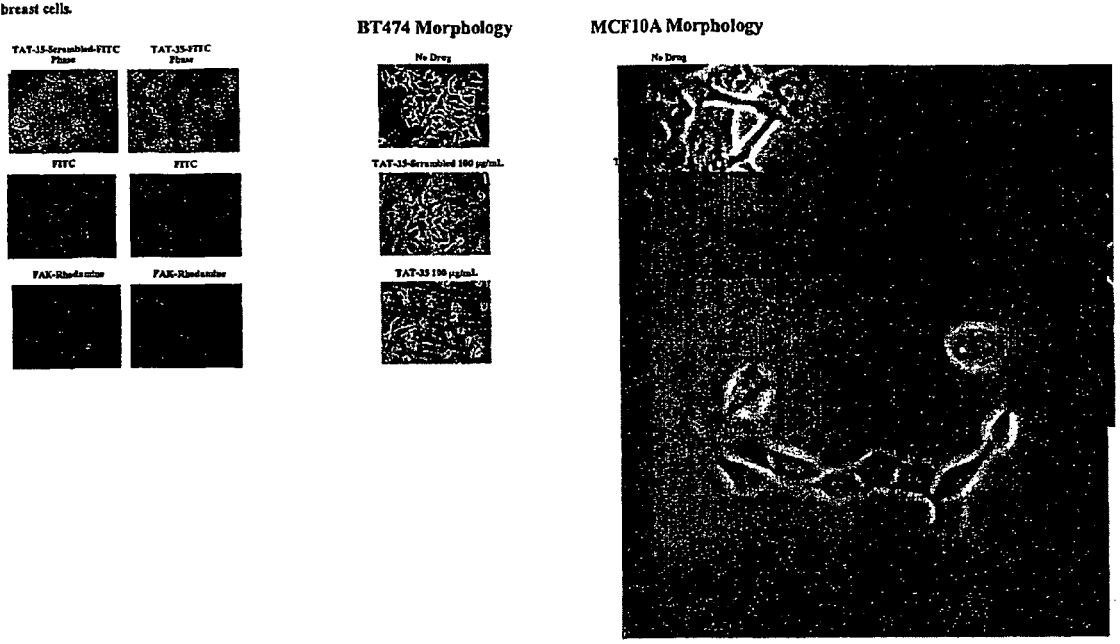
FIG. 3 is a series of photomicrographs showing that peptide-35, but not scrambled peptide-35, caused displacement of FAK from focal adhesions in BT474, BT20, and MCF7 cells; and that peptide-35 caused rounding and detachment in BT474 cells, but not in normal MCF10A breast cells.
Figure 4:
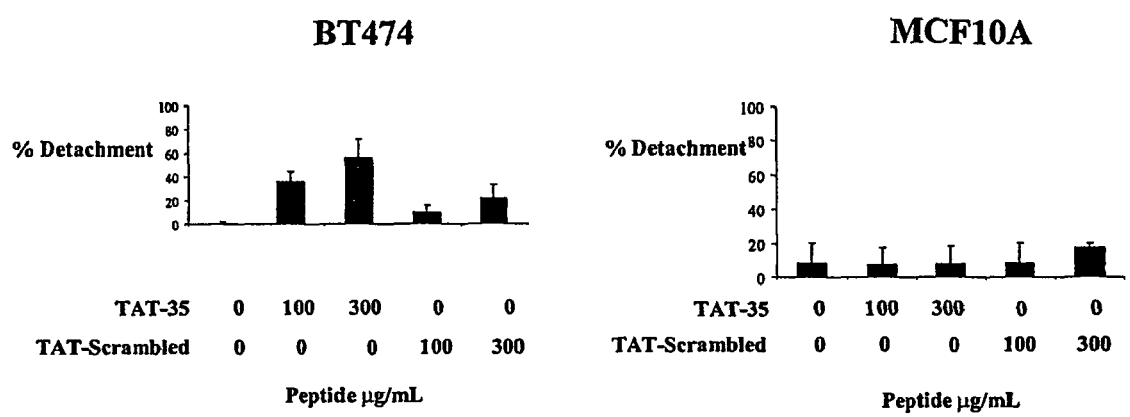
FIG. 4 is two graphs showing that peptide-35 caused a higher level of detachment in BT474 cancer cells when compared with the control, scrambled peptide-35; and that peptide-35 and scrambled peptide caused minimal detachment in normal MCF10A breast cells.
Figure 5:
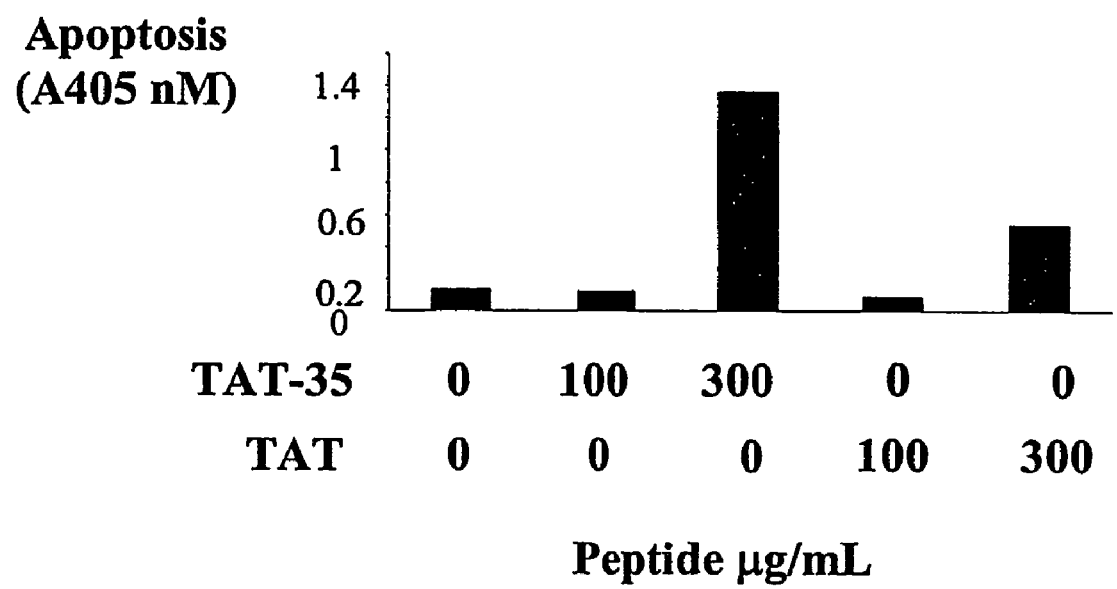
FIG. 5 is graph showing that peptide-35 caused a higher level of apoptosis in BT474 cells when compared with the control, TAT.
Figure 6:
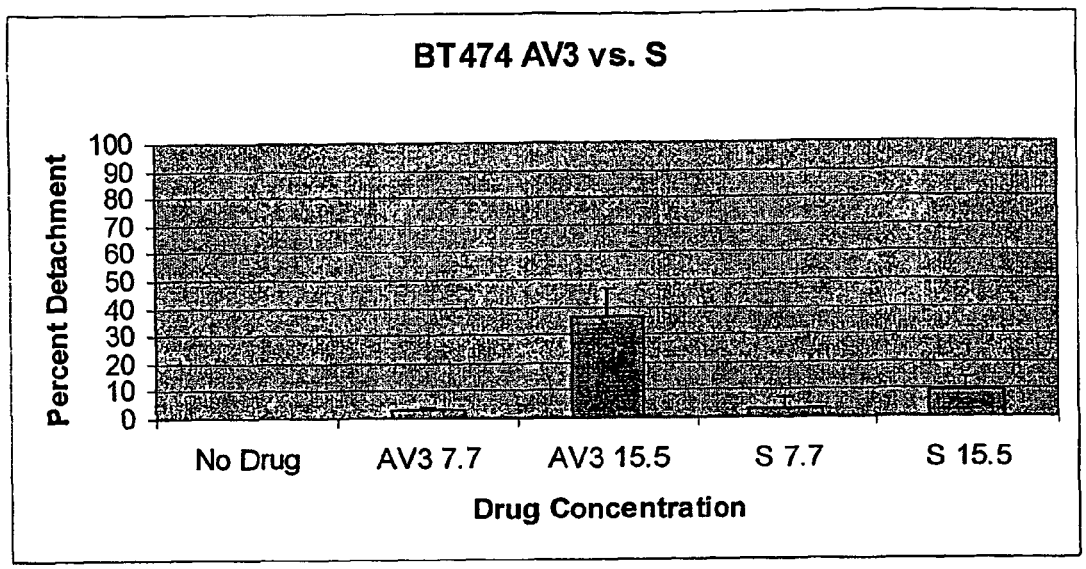
FIG. 6 is a graph showing percent attachment of cells in the presence of different concentrations of AV3.
Figure 7:
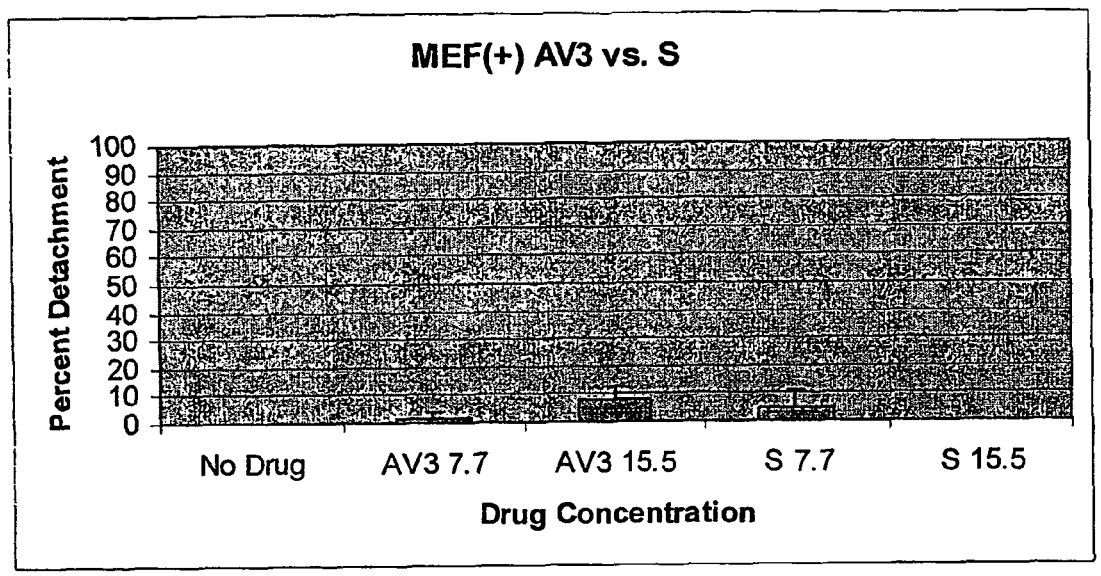
FIG. 7 is a graph showing percent attachment of cells in the presence of different concentrations of AV3 and scrambled AV3 (S).
Figure 8:
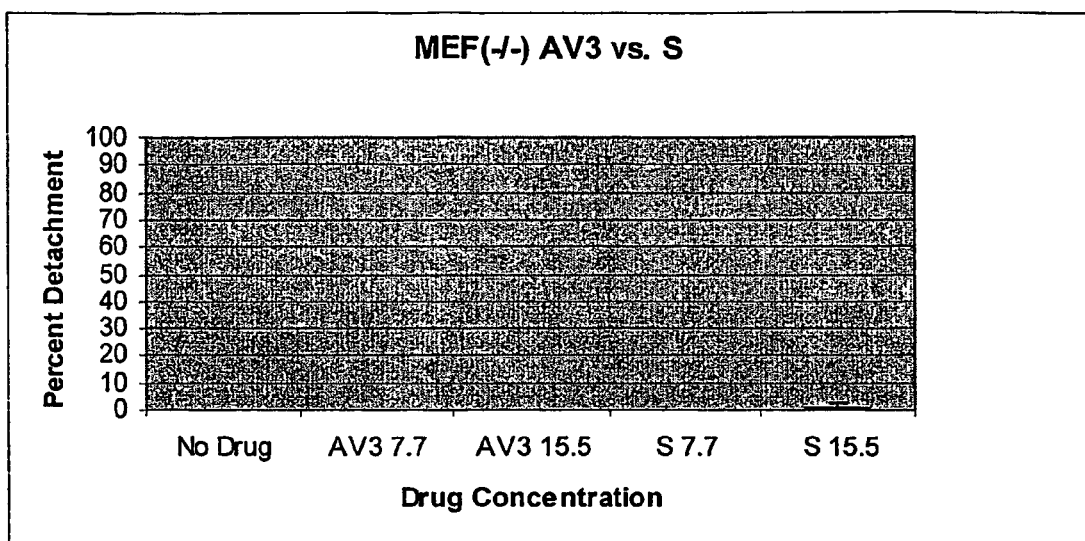
FIG. 8 is a graph showing percent detachment of cells in the presence of different concentrations of AV3 and scrambled AV3 (S).
Figure 9:
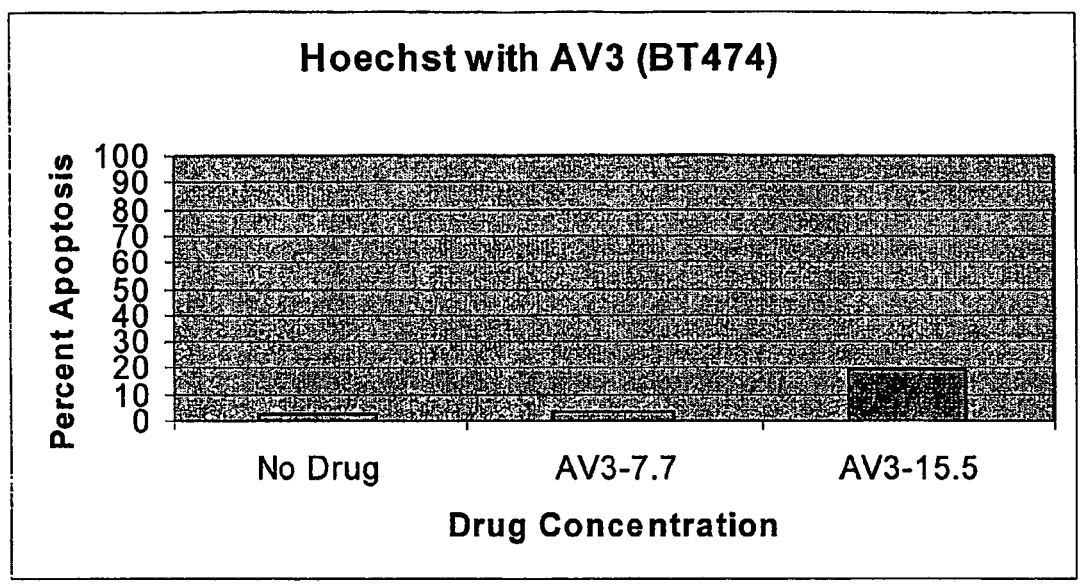
FIG. 9 is a graph showing percent apoptosis of cells in the presence of different concentrations of AV3.
Figure 10:
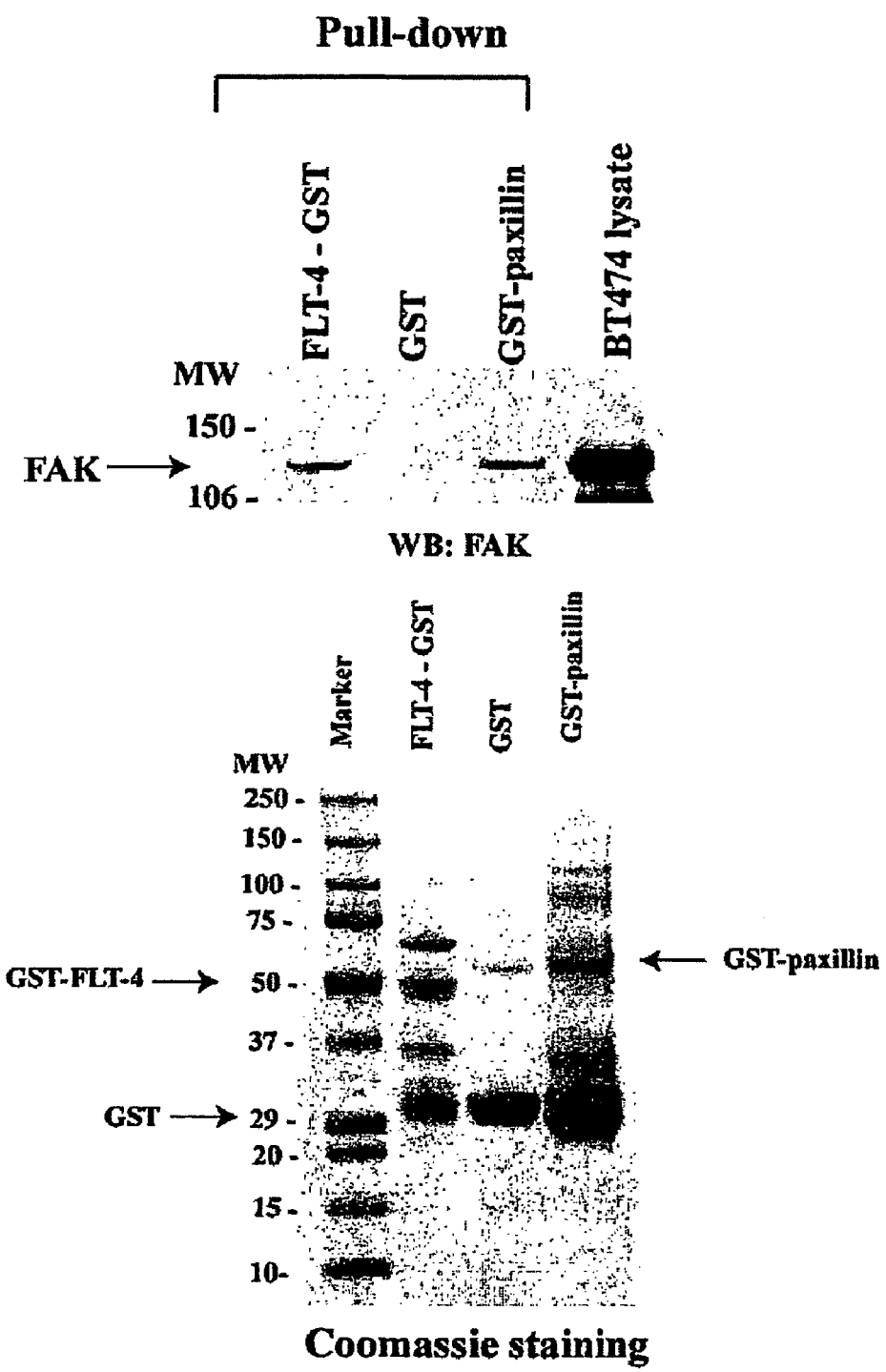
FIG. 10 are two gels showing the results of binding of VEGFR-3/FLT-4 by pull-down assay.
Figure 11:
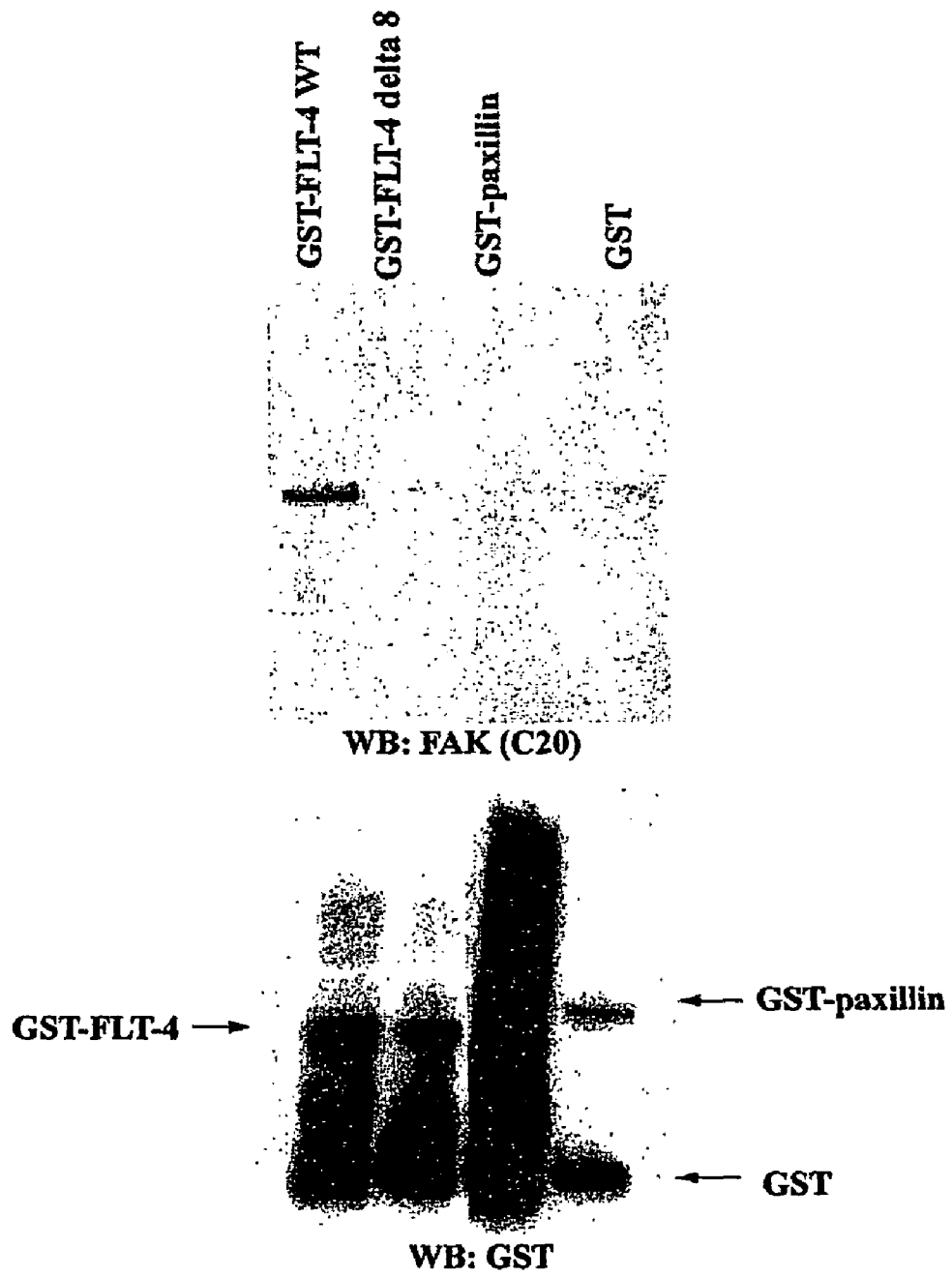
FIG. 11 is a blot showing direct binding of C-terminal FAK, FAK-CD with VEGFR-3/FLT-4 wild type and not with the mutant FLT-4 with deleted 8 amino-acids homologous to peptide 35.

In a preferred embodiment, molecules binding FAK or FAT are provided. The invention features a variety of molecules that specifically bind FAK or FAT. Such molecules preferably modulate a physiological response in a cell in which FAK normally occurs (e.g., a cancer cell such as one in an in vitro culture or in an animal subject). The physiological response may be related to adherence (e.g., to plastic or ECM components), intracellular localization of FAK (e.g., at or not at a focal adhesion), prevention of apoptosis, tyrosine kinase activity, or interaction of FAK with other endogenous molecules such as paxillin or talin. Molecules that specifically bind FAK or FAT may take the form of a peptide (e.g., a cyclic peptide), a protein mimetic, an antibody, or a small organic or inorganic molecule. Whether a given molecule specifically binds FAK or FAT and causes a physiological response in a cell can be determined empirically by the methods described infra. For example, peptides that bind the C-terminus of FAK were identified using phage display techniques. Peptide-32 bound FAK-CD and contained the LD paxillin-binding motif that validated the phage display technique (FIG. 1). Peptide-35 is a twelve amino-acid peptide that binds to specific sequences of FAK-CD (FIG. 2). Peptide-35, coupled to TAT- FITC, was able to penetrate breast cancer cells and cause displacement of FAK from focal adhesions, degradation of FAK, rounding, and detachment in BT474, BT20, and MCF7 breast cancer cells, but not in normal MCF10A cells (FIG. 3). Peptide-35 caused detachment and apoptosis in BT474 breast cancer cells, but not in MCF10A normal breast cells (FIGS. 4 and 5).

Preliminary phage display assays also identified peptide 35 (SEQ ID NO: 1) that binds to the C-terminal part of FAK and FAT domain. Peptide-35 caused loss of focal adhesions and apoptosis in cancer cells, but not in normal mammary cancer cell lines, identifying it as a therapeutic drug in cancer cells. BLAST search with peptide-35 detected that this peptide is homologous to a peptide from VEGFR-3 (vascular endothelial growth factor receptor-3) or FLT-4 gene. The synthesized VEGFR-3 (AV-3) (SEQ ID NO: 3) peptide caused apoptosis in cancer cells similar to peptide 35. Based on the data, AV-3 peptide (homologous to the twelve amino-acids of VEGFR-3), conjugated with TAT peptide for penetration into cells increased detachment and apoptosis in IMR neuroblastoma cells which express high levels of VEGFR-3.

FAK-Binding Peptides and Variants Thereof

A presently preferred molecule that specifically binds FAK or FAT is one in the form of a peptide, e.g., peptide 35 (SEQ ID NO: 1), AV3 (SEQ ID NO: 3) or variants of peptide 35 (e.g., mutants or mimetics). Peptide 35 was identified using a phage display method as described below. It is 12 amino acid residues in length (WHWQWTPWSIQP; SEQ ID NO:1).

The peptide 35 mutants within the invention differ by one or more amino acids from native peptide 35. For example, peptide 35 mutants within the invention can have about 70% or more (e.g., 75, 80, 85, 90, or 95%) sequence identity with native peptide 35. Examples of peptide 35 mutants include those that feature a substitution of one of the amino acid residues that occurs in native peptide 35. Other peptide 35 and AV3 mutants within the invention are those with two or more (e.g., 3, 4, 5, or more) such amino acid substitutions, as well as deletion (e.g., truncation) and addition (i.e., those with additional amino acids added to the native peptide 35 (SEQ ID NO: 1) and AV3 (SEQ ID NO: 3) sequence mutations. Those that retain specific binding to FAK and/or the ability to exert a physiological response in a FAK-containing cell are preferred; albeit those that do not may also be useful (e.g., for use as controls).

Mutants of peptide 35 and AV3 can be made in a number of ways by adapting techniques well known in the art. See, e.g., Sambrook et al., supra; and Ausubel et al., supra. For example, starting with the known amino acid sequence of peptide 35 (i.e., SEQ ID NO: 1), the skilled artisan can chemically synthesize various mutant peptide 35 molecules using, e.g., automated commercial polypeptide synthesizers. Techniques for solid phase synthesis of polypeptides are well known. See, e.g., Barany and Merrifield, *Solid-Phase Peptide Synthesis*; pp. 3-284 in *The Peptides: Analysis, Synthesis, Biology. Vol. 2: Special Methods in Peptide Synthesis, Part A*., Merrifield, et al., *J. Am. Chem. Soc.*, 85: 2149-2156 (1963), and Stewart et al., *Solid Phase Peptide Synthesis*, 2nd ed. Pierce Chem. Co., Rockford, Ill. (1984). Using this technique, peptide 35 mutants can be synthesized as a single polypeptide.

Mutants of peptide 35 (SEQ ID NO: 1) and AV3 (SEQ ID NO: 3) can also be produced through recombinant expression of peptide 35-encoding nucleic acids (see below) in which the nucleic acid is modified, randomly or in a site-specific manner, to change (substitute), add to, or delete, some or all of the amino acids in the encoded polypeptide. Site-specific mutations can be introduced by a variety of conventional techniques well described in the scientific and patent literature. Illustrative examples include: site-directed mutagenesis by overlap extension polymerase chain reaction (OE-PCR), as in Urban (1997) *Nucleic Acids Res.* 25: 2227-2228; Ke (1997) *Nucleic Acids Res.*, 25: 3371-3372, and Chattopadhyay (1997) *Biotechniques* 22: 1054-1056, describing PCR-based site-directed mutagenesis "megaprimer" method; Bohnsack (1997) *Mol. Biotechnology.* 7: 181-188; Ailenberg (1997) *Biotechniques* 22: 624-626, describing site-directed mutagenesis using a PCR-based staggered re-annealing method without restriction enzymes; Nicolas (1997) *Biotechniques* 22: 430-434, site-directed mutagenesis using long primer-unique site elimination and exonuclease III. Unique-site elimination mutagenesis can also be used (see, e.g., Dang et al. (1992) *Anal. Biochem.*, 200: 81).

Other peptide 35 and AV3 (SEQ ID NO: 3) mutants can be prepared by chemically modifying native peptide 35 (SEQ ID NO: 1) and AV3 (SEQ ID NO: 3) according to known chemical modification methods. See, e.g., Belousov (1997) *Nucleic Acids Res.* 25:3440-3444; Frenkel (1995) *Free Radic. Biol Med.* 19: 373-380; Blommers (1994) Biochemistry 33: 7886-7896. Likewise, peptide 35 and AV3 mutants made by chemical synthesis or by expression of nucleic acids as described above can be chemically modified to make additional peptide 35 and AV3 mutants.

Nucleic Acid Encoding Molecules that Specifically Bind FAK or FAT.

Included within the scope of this invention are the functional equivalents of the herein-described isolated nucleic acid molecules. The degeneracy of the genetic code permits substitution of certain codons by other codons which specify the same amino acid and hence would give rise to the same protein. The nucleic acid sequence can vary substantially since, with the exception of methionine and tryptophan, the known amino acids can be coded for by more than one codon. Thus, portions or all of the peptide 35 and AV3 gene could be synthesized to give a nucleic acid sequence significantly different from that shown in SEQ ID NO: 1 and SEQ ID NO: 3.

In addition, the nucleic acid sequence may comprise a nucleotide sequence which results from the addition, deletion or substitution of at least one nucleotide to the 5'-end and/or the 3'-end of the nucleic acid formula shown in SEQ ID NO: 1 and SEQ ID NO: 3 or a derivative thereof. Any nucleotide or polynucleotide may be used in this regard. For example, the present invention is intended to include any nucleic acid sequence resulting from the addition of ATG as an initiation codon at the 5'-end of the inventive nucleic acid sequence or its derivative, or from the addition of TTA, TAG or TGA as a termination codon at the 3'-end of the inventive nucleotide sequence or its derivative. Moreover, the nucleic acid molecule of the present invention may, as necessary, have restriction endonuclease recognition sites added to its 5'-end and/or 3'-end.

Such functional alterations of a given nucleic acid sequence afford an opportunity to promote secretion and/or processing of heterologous proteins encoded by foreign nucleic acid sequences fused thereto. All variations of the nucleotide sequence of the FAT and/or FAK binding genes and fragments thereof permitted by the genetic code are, therefore, included in this invention.

Further, it is possible to delete codons or to substitute one or more codons by codons other than degenerate codons to produce a structurally modified polypeptide, but one which has substantially the same utility or activity of the polypeptide produced by the unmodified nucleic acid molecule. As recognized in the art, the two polypeptides are functionally equivalent, as are the two nucleic acid molecules which give rise to their production, even though the differences between the nucleic acid molecules are not related to degeneracy of the genetic code.

Nucleic Acid Probes for the Detection of FAK Binding Molecules

A nucleic acid probe of the present invention may be used to probe an appropriate phage display, chromosomal or cDNA library by usual hybridization methods to obtain another nucleic acid molecule of the present invention. A phage display, chromosomal DNA or cDNA library may be prepared from appropriate cells according to recognized methods in the art and as described in detail in the Examples which follow (cf. Molecular Cloning: A Laboratory Manual, second edition, edited by Sambrook, Fritsch, & Maniatis, Cold Spring Harbor Laboratory, 1989).

In the alternative, chemical synthesis is carried out in order to obtain nucleic acid probes having nucleotide sequences which correspond to N-terminal and C-terminal portions of the amino acid sequence of the polypeptide of interest. Thus, the synthesized nucleic acid probes may be used as primers in a polymerase chain reaction (PCR) carried out in accordance with recognized PCR techniques, essentially according to PCR Protocols, A Guide to Methods and Applications, edited by Michael et al., Academic Press, 1990, utilizing the appropriate phage display, chromosomal or cDNA library to obtain the fragment of the present invention.

One skilled in the art can readily design such probes based on the sequence disclosed herein using methods of computer alignment and sequence analysis known in the art (cf. Molecular Cloning: A Laboratory Manual, second edition, edited by Sambrook, Fritsch, & Maniatis, Cold Spring Harbor Laboratory, 1989). The hybridization probes can be labeled by standard labeling techniques such as with a radiolabel, enzyme label, fluorescent label, biotin-avidin label, chemiluminescence, and the like. After hybridization, the probes may be visualized using known methods.

The nucleic acid probes include RNA, as well as DNA probes, such probes being generated using techniques known in the art. The nucleic acid probe may be immobilized on a solid support. Examples of such solid supports include, but are not limited to, plastics such as polycarbonate, complex carbohydrates such as agarose and sepharose, and acrylic resins, such as polyacrylamide and latex beads. Techniques for coupling nucleic acid probes to such solid supports are well known in the art.

The test samples suitable for nucleic acid probing methods of the present invention include, for example, cells or nucleic acid extracts of cells, or biological fluids. The sample used will vary based on the assay format, the detection method and the nature of the tissues, cells or extracts to be assayed. Methods for preparing nucleic acid extracts of cells are well known in the art and can be readily adapted in order to obtain a sample which is compatible with the method utilized.

Probe Based Method and Kit for Detection of FAK Binding Molecules

One method of detecting the presence of FAK in a sample comprises a) contacting a sample with a nucleic acid probe, under conditions such that hybridization occurs, and b) detecting the presence of the probe bound to the nucleic acid molecule. One skilled in the art would select the nucleic acid probe according to techniques known in the art as described above. Samples to be tested include but should not be limited to samples of human cells and tissue.

A kit for detecting the presence of detecting FAK binding molecules in a sample comprises at least one container means having disposed therein a nucleic acid probe. The kit may further comprise other containers comprising one or more of the following: wash reagents and reagents capable of detecting the presence of bound nucleic acid probe. Examples of detection reagents include, but are not limited to radiolabeled probes, enzymatic labeled probes (horse radish peroxidase, alkaline phosphatase), and affinity labeled probes (biotin, avidin, or streptavidin).

In detail, a compartmentalized kit includes any kit in which reagents are contained in separate containers. Such containers include small glass containers, plastic containers or strips of plastic or paper. Such containers allow the efficient transfer of reagents from one compartment to another compartment such that the samples and reagents are not cross-contaminated and the agents or solutions of each container can be added in a quantitative fashion from one compartment to another. Such containers will include a container which will accept the test sample, a container which contains the probe or primers used in the assay, containers which contain wash reagents (such as phosphate buffered saline, Tris-buffers, and the like), and containers which contain the reagents used to detect the hybridized probe, bound antibody, amplified product, or the like. One skilled in the art will readily recognize that the nucleic acid probes described in the present invention can readily be incorporated into one of the established kit formats which are well known in the art.

Constructs Expressing a FAK and/or FAT Binding Peptide

The present invention also relates to a recombinant DNA molecule comprising, 5' to 3', a promoter effective to initiate transcription in a host cell and nucleic acid molecules expressing FAK and/or FAT binding peptides. In addition, the present invention relates to a recombinant DNA molecule comprising a vector and an above-described nucleic acid molecule. The present invention also relates to a nucleic acid molecule comprising a transcriptional region functional in a cell, a sequence complimentary to an RNA sequence encoding an amino acid sequence corresponding to the above-described polypeptide, and a transcriptional termination region functional in a host cell. The molecules may be isolated and/or purified DNA molecules.

The present invention also relates to a cell or organism comprising nucleic acid molecules encoding peptides binding to FAT and/or FAK and modulate apoptosis, motility and/or invasion (metastasis). The peptide may be purified from cells which have been altered to express the peptide. A cell is said to be "altered to express a desired peptide" when the cell, through genetic manipulation, is made to produce a protein which it normally does not produce or which the cell normally produces at lower levels. One skilled in the art can readily adapt procedures for introducing and expressing either genomic, cDNA, or synthetic sequences into either eukaryotic or prokaryotic cells.

A nucleic acid molecule, such as DNA, is said to be "capable of expressing" a polypeptide if it comprises nucleotide sequences which contain transcriptional and translational regulatory information and such sequences are "operably linked" to nucleotide sequences which encode the polypeptide. An operable linkage is a linkage in which the regulatory DNA sequences and the DNA sequence sought to be expressed are connected in such a way as to permit gene sequence expression. The precise nature of the regulatory regions needed for gene sequence expression may vary from organism to organism, but shall in general include a promoter region which, in prokaryotes, contains both the promoter (which directs the initiation of RNA transcription) as well as the DNA sequences which, when transcribed into RNA, will signal synthesis initiation. Such regions will normally include those 5'-non-coding sequences involved with initiation of transcription and translation, such as the TATA box, capping sequence, CAAT sequence, and the like.

If desired, the non-coding region 3' to the sequence encoding a FAT and/or FAK binding peptide may be obtained by the above-described methods. This region may be retained for its transcriptional termination regulatory sequences, such as termination and polyadenylation. Thus, by retaining the 3'-region naturally contiguous to the DNA sequence encoding a FAT and/or FAK binding peptide, the transcriptional termination signals may be provided. Where the transcriptional termination signals are not satisfactorily functional in the expression host cell, then a 3' region functional in the host cell may be substituted.

Two DNA sequences (such as a promoter region sequence and a nucleic acid sequence encoding for example an FAK binding peptide) are said to be operably linked if the nature of the linkage between the two DNA sequences does not (1) result in the introduction of a frame-shift mutation, (2) interfere with the ability of the promoter region sequence to direct the transcription of an FAT and/or FAK peptide binding gene sequence, or (3) interfere with the ability of a gene sequence encoding an FAT and/or FAK binding peptide, to be transcribed by the promoter region sequence. Thus, a promoter region would be operably linked to a DNA sequence if the promoter were capable of effecting transcription of that DNA sequence.

The present invention also encompasses the expression of nucleic acid molecules encoding FAK and/or FAT binding peptides (or a functional derivatives thereof) in either prokaryotic or eukaryotic cells. Prokaryotic hosts are, generally, very efficient and convenient for the production of recombinant proteins and are, therefore, one type of preferred expression system for the FAT and/or FAK binding molecules. Prokaryotes most frequently are represented by various strains of *E. coli*. However, other microbial strains may also be used, including other bacterial strains.

In prokaryotic systems, plasmid vectors that contain replication sites and control sequences derived from a species compatible with the host may be used. Examples of suitable plasmid vectors may include pBR322, pUC118, pUC119 and the like; suitable phage or bacteriophage vectors may include γgt10, γgt11 and the like; and suitable virus vectors may include pMAM-neo, pKRC and the like. Preferably, the selected vector of the present invention has the capacity to replicate in the selected host cell.

Recognized prokaryotic hosts include bacteria such as *E. coli, Bacillus, Streptomyces, Pseudomonas, Salmonella, Serratia*, and the like. However, under such conditions, the peptide will not be glycosylated. The prokaryotic host must be compatible with the replicon and control sequences in the expression plasmid.

To express nucleic acid molecules encoding FAT and/or FAK peptide binding molecules (or a functional derivative thereof) in a prokaryotic cell, it is necessary to operably link the desired sequences to a functional prokaryotic promoter. Such promoters may be either constitutive or, more preferably, regulatable (e.g., inducible). Examples of constitutive promoters include the int promoter of bacteriophage λ, the bla promoter of the β-lactamase gene sequence of pBR322, and the CAT promoter of the chloramphenicol acetyl transferase gene sequence of pPR325, and the like. Examples of inducible prokaryotic promoters include the major right and left promoters of bacteriophage λ ($P_L$ and $P_R$), the trp, recA, lacZ, lacI, and gal promoters of *E. coli*, the α-amylase (Ulmanen et al., *J. Bacteriol.* 162:176-182 (1985)) and the ξ-28-specific promoters of *B. subtilis* (Gilman et al., *Gene Sequence* 32:11-20 (1984)), the promoters of the bacteriophages of *Bacillus* (Gryczan, In: The Molecular Biology of the Bacilli, Academic Press, Inc., New York (1982)), and *Streptomyces* promoters (Ward et al., *Mol. Gen. Genet.* 203:468-478 (1986)). Prokaryotic promoters are reviewed by Glick (*J. Ind. Microbiol.* 1:277-282 (1987)); Cenatiempo (*Biochimie* 68:505-516 (1986)); and Gottesman (*Ann. Rev. Genet.* 18:415-442 (1984)).

Proper expression in a prokaryotic cell also requires the presence of a ribosome binding site upstream of the gene sequence-encoding sequence. Such ribosome binding sites are disclosed, for example, by Gold et al. (*Ann. Rev. Microbiol.* 35:365-404 (1981)). The selection of control sequences, expression vectors, transformation methods, and the like, are dependent on the type of host cell used to express the gene. As used herein, "cell", "cell line", and "cell culture" may be used interchangeably and all such designations include progeny. Thus, the words "transformants" or "transformed cells" include the primary subject cell and cultures derived therefrom, without regard to the number of transfers. It is also understood that all progeny may not be precisely identical in DNA content, due to deliberate or inadvertent mutations. However, as defined, mutant progeny have the same functionality as that of the originally transformed cell.

Host cells which may be used in the expression systems of the present invention are not strictly limited, provided that they are suitable for use in the expression of the peptides of interest. Suitable hosts may often include eukaryotic cells. Preferred eukaryotic hosts include, for example, yeast, fungi, insect cells, mammalian cells either in vivo, or in tissue culture. Mammalian cells which may be useful as hosts include HeLa cells, cells of fibroblast origin such as VERO or CHO-K1, or cells of lymphoid origin and their derivatives. Preferred mammalian host cells include SP2/0 and J558L, as well as neuroblastoma cell lines such as IMR 332 which may provide better capacities for correct post-translational processing.

In addition, plant cells are also available as hosts, and control sequences compatible with plant cells are available, such as the cauliflower mosaic virus 35S and 19S, and nopaline synthase promoter and polyadenylation signal sequences. Another preferred host is an insect cell, for example the *Drosophila* larvae. Using insect cells as hosts, the *Drosophila* alcohol dehydrogenase promoter can be used. Rubin, *Science* 240:1453-1459 (1988). Alternatively, baculovirus vectors can be engineered to express large amounts of nucleic acid molecules encoding FAT and/or FAK binding peptides in insects cells (Jasny, *Science* 238:1653 (1987); Miller et al., In: *Genetic Engineering* (1986), Setlow, J. K., et al., eds., Plenum, Vol. 8, pp. 277-297).

Any of a series of yeast gene sequence expression systems can be utilized which incorporate promoter and termination elements from the actively expressed gene sequences coding for glycolytic enzymes are produced in large quantities when yeast are grown in mediums rich in glucose. Known glycolytic gene sequences can also provide very efficient transcriptional control signals. Yeast provides substantial advantages in that it can also carry out post-translational peptide modifications. A number of recombinant DNA strategies exist which utilize strong promoter sequences and high copy number of plasmids which can be utilized for production of the desired proteins in yeast. Yeast recognizes leader sequences on cloned mammalian gene sequence products and secretes peptides bearing leader sequences (i.e., pre-peptides). For a mammalian host, several possible vector systems are available.

A wide variety of transcriptional and translational regulatory sequences may be employed, depending upon the nature of the host. The transcriptional and translational regulatory signals may be derived from viral sources, such as adenovirus, bovine papilloma virus, cytomegalovirus, simian virus, or the like, where the regulatory signals are associated with a particular gene sequence which has a high level of expression. Alternatively, promoters from mammalian expression products, such as actin, collagen, myosin, and the like, may be employed. Transcriptional initiation regulatory signals may be selected which allow for repression or activation, so that expression of the gene sequences can be modulated. Of interest are regulatory signals which are temperature-sensitive so that by varying the temperature, expression can be repressed or initiated, or are subject to chemical (such as metabolite) regulation.

Expression of nucleic acids encoding peptides that bind to FAT and/or FAK in eukaryotic hosts requires the use of eukaryotic regulatory regions. Such regions will, in general, include a promoter region sufficient to direct the initiation of RNA synthesis. Preferred eukaryotic promoters include, for example, the promoter of the mouse metallothionein I gene sequence (Hamer et al., *J. Mol. Appl. Gen.* 1:273-288 (1982)); the TK promoter of Herpes virus (McKnight, *Cell* 31:355-365 (1982)); the SV40 early promoter (Benoist et al., *Nature* (London) 290:304-310 (1981)); the yeast gal4 gene sequence promoter (Johnston et al., *Proc. Natl. Acad. Sci.* (USA) 79:6971-6975 (1982); Silver et al., *Proc. Natl. Acad. Sci.* (USA) 81:5951-5955 (1984)).

Translation of eukaryotic mRNA is initiated at the codon which encodes the first methionine. If a chimeric fusion molecule is desired, it is preferable to ensure that the linkage between a eukaryotic promoter and a DNA sequence which encodes peptides binding to FAT and/or FAK (or a functional derivative thereof) contain intervening codons which are capable of encoding a methionine (i.e., AUG). The presence of such codons results either in a formation of a fusion protein (if the AUG codon is in the same reading frame as the desired nucleic acid molecule coding sequence) or a frame-shift mutation (if the AUG codon is not in the same reading frame as the desired nucleic acid coding sequence).

A desired nucleic acid molecule and an operably linked promoter may be introduced into a recipient prokaryotic or eukaryotic cell either as a nonreplicating DNA (or RNA) molecule, which may either be a linear molecule or, more preferably, a closed covalent circular molecule. Since such molecules are incapable of autonomous replication, the expression of the gene may occur through the transient expression of the introduced sequence. Alternatively, permanent expression may occur through the integration of the introduced DNA sequence into the host chromosome.

A vector may be employed which is capable of integrating the desired gene sequences into the host cell chromosome. Cells which have stably integrated the introduced DNA into their chromosomes can be selected by also introducing one or more markers which allow for selection of host cells which contain the expression vector. The marker may provide for prototrophy to an auxotrophic host, biocide resistance, e.g., antibiotics, or heavy metals, such as copper, or the like. The selectable marker gene sequence can either be directly linked to the DNA gene sequences to be expressed, or introduced into the same cell by co-transfection. Additional elements may also be needed for optimal synthesis of single chain binding protein mRNA. These elements may include splice signals, as well as transcription promoters, enhancers, and termination signals. cDNA expression vectors incorporating such elements include those described by Okayama, *Mol. Cell. Biol.* 3:280 (1983).

The introduced nucleic acid molecule can be incorporated into a plasmid or viral vector capable of autonomous replication in the recipient host. Any of a wide variety of vectors may be employed for this purpose. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species. Preferred prokaryotic vectors include plasmids such as those capable of replication in *E. Coli* (such as, for example, pBR322, ColE1, pSC101, pACYC 184, πVX. Such plasmids are, for example, disclosed by Sambrook (cf. Molecular Cloning: A Laboratory Manual, second edition, edited by Sambrook, Fritsch, & Maniatis, Cold Spring Harbor Laboratory, (1989)). *Bacillus* plasmids include pC194, pC221, pT127, and the like. Such plasmids are disclosed by Gryczan (In: The Molecular Biology of the Bacilli, Academic Press, New York (1982), pp. 307-329). Suitable *Streptomyces* plasmids include p1J101 (Kendall et al., *J. Bacteriol.* 169: 4177-4183 (1987)), and *Streptomyces* bacteriophages such as φC31 (Chater et al., In: Sixth International Symposium on Actinomycetales Biology, Akademiai Kaido, Budapest, Hungary (1986), pp. 45-54). *Pseudomonas* plasmids are reviewed by John et al. (*Rev. Infect. Dis.* 8:693-704 (1986)).

Preferred eukaryotic plasmids include, for example, BPV, vaccinia, SV40, 2-micron circle, and the like, or their derivatives. Such plasmids are well known in the art (Botstein et al., Miami Wntr. Symp. 19:265-274 (1982); Broach, In: The Molecular Biology of the Yeast *Saccharomyces*: Life Cycle and Inheritance, Cold Spring Harbor Laboratory, Cold Spring Harbor, N.Y., p. 445-470 (1981); Broach, Cell 28:203-204 (1982); Bollon et al., *J. Clin. Hematol. Oncol.* 10:39-48 (1980); Maniatis, In: Cell Biology: A Comprehensive Treatise, Vol. 3, Gene Sequence Expression, Academic Press, New York, pp. 563-608 (1980).

Once the vector or nucleic acid molecule comprising the construct(s) has been prepared for expression, the DNA construct(s) may be introduced into an appropriate host cell by any of a variety of suitable means, i.e., transformation, transfection, conjugation, protoplast fusion, electroporation, particle gun technology, calcium phosphate-precipitation, direct microinjection, and the like. After the introduction of the vector, recipient cells are grown in a selective medium, which selects for the growth of vector-containing cells. Expression of the cloned gene molecule(s) results in the production of desired nucleic acid molecules or fragments thereof. This can take place in the transformed cells as such, or following the induction of these cells to differentiate (for example, by administration of bromodeoxyuracil to neuroblastoma cells or the like). A variety of incubation conditions can be used to form the peptides of the present invention. The most preferred conditions are those which mimic physiological conditions.

Purified Polypeptides.

A variety of methodologies known in the art can be utilized to obtain the peptide of the present invention. One skilled in the art can readily follow known methods for isolating proteins in order to obtain the peptide free of natural contaminants. These include, but are not limited to: size-exclusion chromatography, HPLC, ion-exchange chromatography, and immuno-affinity chromatography.

Antibody and Hybridoma.

The present invention relates to an antibody having binding affinity to an FAT and/or FAK binding polypeptides. The polypeptide may have the amino acid sequence set forth in SEQ ID NO: 1, SEQ ID NO: 3 or mutant or species variation thereof, or at least 9 contiguous amino acids thereof (preferably, at least 10, 15, 20, or 30 contiguous amino acids thereof).

The present invention also relates to an antibody having specific binding affinity to an FAT and/or FAK binding polypeptide. Such an antibody may be isolated by comparing its binding affinity to an FAT and/or FAK binding polypeptide with its binding affinity to another polypeptide. Those which bind selectively to an FAT and/or FAK binding would be chosen for use in methods requiring a distinction between an FAT and/or FAK binding and other polypeptides. Such methods could include, but should not be limited to, the analysis of altered FAT and/or FAK binding peptide expression in tissue containing other polypeptides such as VEGFR-3, short and long form FLT-4 and the like.

The proteins of the present invention can be used in a variety of procedures and methods, such as for the generation of antibodies, for use in identifying pharmaceutical compositions, and for studying DNA/protein interaction. Peptides, such as for example, SEQ ID NO: 1 and seq id 3 can be used to produce antibodies or hybridomas. One skilled in the art will recognize that if an antibody is desired, such a peptide would be generated as described herein and used as an immunogen. The antibodies of the present invention include monoclonal and polyclonal antibodies, as well fragments of these antibodies, and humanized forms. Humanized forms of the antibodies of the present invention may be generated using one of the procedures known in the art such as chimerization or CDR grafting. The present invention also relates to a hybridoma which produces the above-described monoclonal antibody, or binding fragment thereof. A hybridoma is an immortalized cell line which is capable of secreting a specific monoclonal antibody.

In general, techniques for preparing monoclonal antibodies and hybridomas are well known in the art (Campbell, "Monoclonal Antibody Technology: Laboratory Techniques in Biochemistry and Molecular Biology," Elsevier Science Publishers, Amsterdam, The Netherlands (1984); St. Groth et al., *J. Immunol. Methods* 35:1-21 (1980)). Any animal (mouse, rabbit, and the like) which is known to produce antibodies can be immunized with the selected polypeptide. Methods for immunization are well known in the art. Such methods include subcutaneous or intraperitoneal injection of the polypeptide. One skilled in the art will recognize that the amount of polypeptide used for immunization will vary based on the animal which is immunized, the antigenicity of the polypeptide and the site of injection.

The polypeptide may be modified or administered in an adjuvant in order to increase the peptide antigenicity. Methods of increasing the antigenicity of a polypeptide are well known in the art. Such procedures include coupling the antigen with a heterologous protein (such as globulin or β-galactosidase) or through the inclusion of an adjuvant during immunization.

For monoclonal antibodies, spleen cells from the immunized animals are removed, fused with myeloma cells, such as SP2/0-Ag14 myeloma cells, and allowed to become monoclonal antibody producing hybridoma cells. Any one of a number of methods well known in the art can be used to identify the hybridoma cell which produces an antibody with the desired characteristics. These include screening the hybridomas with an ELISA assay, Western blot analysis, or radioimmunoassay (Lutz et al., *Exp. Cell Res.* 175:109-124 (1988)). Hybridomas secreting the desired antibodies are cloned and the class and subclass is determined using procedures known in the art (Campbell, Monoclonal Antibody Technology: Laboratory Techniques in Biochemistry and Molecular Biology, supra (1984)).

For polyclonal antibodies, antibody containing antisera is isolated from the immunized animal and is screened for the presence of antibodies with the desired specificity using one of the above-described procedures. The above-described antibodies may be detectably labeled. Antibodies can be detectably labeled through the use of radioisotopes, affinity labels (such as biotin, avidin, and the like), enzymatic labels (such as horse radish peroxidase, alkaline phosphatase, and the like) fluorescent labels (such as FITC or rhodamine, and the like), paramagnetic atoms, and the like. Procedures for accomplishing such labeling are well-known in the art, for example, see (Sternberger et al., *J. Histochem. Cytochem.* 18:315 (1970); Bayer et al., *Meth. Enzym.* 62:308 (1979); Engval et al., *Immunol.* 109:129 (1972); Goding, *J. Immunol. Meth.* 13:215 (1976)). The labeled antibodies of the present invention can be used for in vitro, in vivo, and in situ assays to identify cells or tissues which express a specific peptide.

The above-described antibodies may also be immobilized on a solid support. Examples of such solid supports include plastics such as polycarbonate, complex carbohydrates such as agarose and sepharose, acrylic resins and such as polyacrylamide and latex beads. Techniques for coupling antibodies to such solid supports are well known in the art (Weir et al., "Handbook of Experimental Immunology" 4th Ed., Blackwell Scientific Publications, Oxford, England, Chapter 10 (1986); Jacoby et al., *Meth. Enzym.* 34 Academic Press, New York (1974)). The immobilized antibodies of the present invention can be used for in vitro, in vivo, and in situ assays as well as in immunochromatography.

Furthermore, one skilled in the art can readily adapt currently available procedures, as well as the techniques, methods and kits disclosed above with regard to antibodies, to generate peptides capable of binding to a specific peptide sequence in order to generate rationally designed anti-peptide peptides, for example see Hurby et al., "Application of Synthetic Peptides Antisense Peptides", In Synthetic Peptides, A User's Guide, W. H. Freeman, N.Y., pp. 289-307 (1992), and Kaspczak et al., *Biochemistry* 28:9230-8(1989).

Anti-peptide peptides can be generated by replacing the basic amino acid residues found in the peptide sequences with acidic residues, while maintaining hydrophobic and uncharged polar groups. For example, lysine, arginine, and/or histidine residues are replaced with aspartic acid or glutamic acid and glutamic acid residues are replaced by lysine, arginine or histidine.

Isolation of Compounds which Interact with FAT, FAK, FAT- and FAK-Binding Peptides The present invention also relates to a method of detecting a compound capable of binding to a FAK, FAT, FAT- and FAK-binding peptides comprising incubating the compound with any one of FAK, FAT, FAT- and FAK-binding peptides and detecting the presence of the bound compound. The compound may be present within a complex mixture, for example, serum, body fluid, or cell extracts. The present invention also relates to a method of detecting an agonist or antagonist of FAK and FAT activity comprising incubating cells that produce FAK and/or FAT in the presence of a compound and detecting changes in the level of FAT and/or FAK activity. The compounds thus identified would produce a change in activity indicative of the presence of the compound. The compound may be present within a complex mixture, for example, serum, body fluid, or cell extracts. Once the compound is identified it can be isolated using techniques well known in the art.

The present invention also encompasses a method of agonizing (stimulating) or antagonizing FAK and/or FAT associated activity in a mammal comprising administering to the mammal an agonist or antagonist to FAK and/or FAT in an amount sufficient to effect an agonism or antagonism.

Compositions

In a preferred embodiment, the activities associated with FAK and/or FAT are modulated by a composition of the invention. For example, apoptosis, motility, invasion are target phenotypes by the compositions. The present invention also relates to compositions and methods for the treatment of disorders which involve modulating the activity and/or level of individual components, and relates to methods for the identification of agents for such treatments. Additionally, the present invention relates to methods and compositions for prognostic evaluation of such disorders.

Described herein are compositions and methods for the prevention, prognostic evaluation, and treatment of disorders described herein, preferably cell proliferative disorders and hematopoietic cell disorders, in which a FAT and/or FAK polypeptides may be involved. Such methods and compositions may include, but are not limited to the agents capable of decreasing or inhibiting the interaction between a FAT and/or FAK polypeptide and a FAT and/or FAK polypeptide binding partner and agents capable of inhibiting or decreasing the activity of such complexes, agents capable of modulating the activity and/or level of individual components of the proteins, and the use and administration of such agents.

Methods for identification of candidate therapeutic agents may include, for example, assays to identify agents capable of disrupting or inhibiting or promoting the interaction between components of the complexes (e.g., AV3/FAT complexes), and may also include paradigms and strategies for the rational design of drugs capable of disruption and/or inhibition and/or promotion of such complexes.

The complexes involved in the invention include a AV3 polypeptide, FAT and/or FAK binding peptides or derivatives thereof. Under standard physiological conditions, the components of such complexes are capable of forming stable, non-covalent attachments with one or more of the other complex components. Methods for the purification and production of such protein complexes, and of cells that exhibit such complexes are described below.

Disruption of Protein Complexes

Disruption of complexes, for example by decreasing or inhibiting the interactions between component members of such a complex may have differing modulatory effects on the event involved, depending on the individual protein complex. "Disruption", as used herein is meant to refer not only to a physical separation of protein complex components, but also refers to a perturbation of the activity of the complexes, regardless of whether or not such complexes remain able, physically, to form. "Activity", as used herein refers to the function of the protein complex in the signal transduction cascade of the cell in which such a complex is formed, i.e., refers to the function of the complex in effecting or inhibiting a transduction of an extracellular signal into a cell. For example, the effect of complex disruption may augment, reduce, or block a signal normally transduced into the cell, thereby modulating apoptosis in a cell. In the case of tumor cells it is desirable to induce apoptosis. Likewise, depending on the disorder involved, either augmentation, reduction, or blockage of a signal normally transduced into the cell will be desirable for the treatment of the disorder.

A disorder involving a complex may, for example, develop because the presence of such a complex brings about the aberrant inhibition of a normal signal transduction event. In such a case, the disruption of the complex would allow the restoration of the usual signal transduction event. Further, an aberrant complex may bring about an altered subcellular adapter protein localization, which may result in, for example, dysfunctional cellular events. An inhibition of the complex in this case would allow for restoration or maintenance of a normal cellular architecture. Still further, an agent or agents that cause(s) disruption of the complex may bring about the disruption of the interactions among other potential components of a complex.

Nucleotide sequences encoding peptide agents which are to be utilized intracellularly may be expressed in the cells of interest, using techniques which are well known to those of ordinary skill in the art. For example, expression vectors derived from viruses such as retroviruses, vaccinia virus, adenoviruses, adeno-associated virus, herpes viruses, or bovine papilloma virus, may be used for delivery and expression of such nucleotide sequences into the targeted cell population. Methods for the construction of such vectors are well known. See, for example, the techniques described in Maniatis et al., 1989, Molecular Cloning: A Laboratory Manual, Cold Spring Harbor Laboratory, N.Y. and in Ausubel et al., Current Protocols in Molecular Biology, Greene Publishing Associates and Wiley Interscience, N.Y. 1989. Complex-binding domains can be identified using, for example, techniques such as those described in Rotin et al. (Rotin et al., *EMBO J.* 11:559-567, 1992), Songyang et al. (Songyang et al., *Cell* 72:767-778, 1993), Felder et al., *Mol. Cell. Biol.* 13:1449-1455, 1993), Fantl et al. (*Cell* 69:413-422, 1992), and Domchek et al. (*Biochemistry* 31:9865-9870, 1992).

Alternatively, antibodies capable of interfering with complex formation may be produced as described below and administered for the treatment of disorders involving a component capable of forming a complex with another protein. Alternatively, nucleotide sequences encoding single-chain antibodies may be expressed within the target cell population by utilizing, for example, techniques such as those described in Marasco et al. (Marasco et al., *Proc. Natl. Acad. Sci. USA* 90:7889-7893, 1993). Agents which act intracellularly to interfere with the formation and/or activity of the protein complexes of the invention may also be small organic or inorganic compounds. A method for identifying these and other intracellular agents is described below.

Antibodies to Complexes

Described herein are methods for the production of antibodies which are capable of specifically recognizing a complex or an epitope thereof, or of specifically recognizing an epitope on either of the components of the complex, especially those epitopes which would not be recognized by the antibody when the component is present separate and apart from the complex. Such antibodies may include, but are not limited to polyclonal antibodies, monoclonal antibodies (mAbs), humanized or chimeric antibodies, single chain antibodies, Fab fragments, F(ab')$_2$ fragments, fragments produced by a Fab expression library, anti-idiotypic (anti-Id) antibodies, and epitope-binding fragments of any of the above. Such antibodies may be used, for example, in the detection of a complex in a biological sample, or, alternatively, as a method for the inhibition of a complex formation, thus inhibiting the development of a disorder.

Polyclonal antibodies are heterogeneous populations of antibody molecules derived from the sera of animals immunized with an antigen, such as a complex, or an antigenic functional derivative thereof. For the production of polyclonal antibodies, various host animals may be immunized by injection with the complex including but not limited to rabbits, mice, rats, etc. Various adjuvants may be used to increase the immunological response, depending on the host species, including but not limited to Freund's (complete and incomplete), mineral gels such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*.

A monoclonal antibody (mAb), which is a substantially homogeneous population of antibodies to a particular antigen, may be obtained by any technique which provides for the production of antibody molecules by continuous cell lines in culture. These include, but are not limited to the hybridoma technique of Kohler and Milstein (*Nature* 256:495-497, 1975) and U.S. Pat. No. 4,376,110), the human B-cell hybridoma technique (Kosbor et al., *Immunology Today* 4:72, 1983; Cole et al., *Proc. Natl. Acad. Sci. USA* 80:2026-2030, 1983), and the EBV-hybridoma technique (Cole et al., Monoclonal Antibodies And Cancer Therapy, Alan R. Liss, Inc., 1985, pp. 77-96). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In addition, techniques developed for the production of "chimeric antibodies" (Morrison et al., *Proc. Natl. Acad. Sci. USA,* 81:6851-6855, 1984; Neuberger et al., *Nature,* 312:604-608, 1984; Takeda et al., *Nature,* 314:452-454, 1985) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region.

Alternatively, techniques described for the production of single chain antibodies (U.S. Pat. No. 4,946,778; Bird, *Science* 242:423-426, 1988; Huston et al., *Proc. Natl. Acad. Sci. USA* 85:5879-5883, 1988; and Ward et al., *Nature* 334:544-546, 1989) can be adapted to produce complex-specific single chain antibodies. Single chain antibodies are formed by linking the heavy and light chain fragment of the $F_v$ region via an amino acid bridge, resulting in a single chain polypeptide.

Antibody fragments which contain specific binding sites of a complex may be generated by known techniques. For example, such fragments include but are not limited to: the $F(ab')_2$ fragments which can be produced by pepsin digestion of the antibody molecule and the Fab fragments which can be generated by reducing the disulfide bridges of the $F(ab')_2$ fragments. Alternatively, Fab expression libraries may be constructed (Huse et al., 1989, *Science,* 246:1275-1281) to allow rapid and easy identification of monoclonal Fab fragments with the desired specificity to the FAT and/or FAK peptide bound complex.

One or more components of a protein complex may be present at a higher than normal cellular level (i.e., higher than the concentration known to usually be present in the cell type exhibiting the protein complex of interest and/or may exhibit an abnormally increased level of cellular activity (i.e., greater than the activity known to usually be present in the cell type exhibiting the protein complex of interest).

For example, the gene encoding a protein complex component may begin to be overexpressed, or may be amplified (i.e., its gene copy number may be increased) in certain cells, leading to an increased number of component molecules within these cells. Additionally, a gene encoding a protein complex component may begin to express a modified protein product that exhibits a greater than normal level of activity. "Activity", refers to the normal cellular function of the component, either enzymatic or structural whose function may include, for example, bringing two or more cellular molecules into the appropriate proximity.

Such an increase in the cellular level and/or activity of a protein complex may lead to the increase in apoptosis of target cells such as tumor cells, decrease in motility and cell invasion. Treatment of such disorders may, therefore, be effectuated by the administration of agents which modulate the cellular level and/or the activity of the protein complex component. For example, techniques for modulating the cellular level and/or the activity of one or more of the protein complex components of interest may include, but are not limited to antisense or ribozyme approaches, and/or gene therapy approaches, each of which is well known to those of skill in the art.

Antisense and Ribozyme Approaches

Included in the scope of the invention are oligoribonucleotides, including antisense RNA and DNA molecules and ribozymes that function to inhibit translation of one or more components of a protein complex. Anti-sense RNA and DNA molecules act to directly block the translation of mRNA by binding to targeted mRNA and preventing protein translation. With respect to antisense DNA, oligodeoxyribonucleotides derived from the translation initiation site, e.g., between −10 and +10 regions of the relevant nucleotide sequence, are preferred.

Ribozymes are enzymatic RNA molecules capable of catalyzing the specific cleavage of RNA. The mechanism of ribozyme action involves sequence specific interaction of the ribozyme molecule to complementary target RNA, followed by a endonucleolytic cleavage. Within the scope of the invention are engineered hammerhead or other motif ribozyme molecules that specifically and efficiently catalyze endonucleolytic cleavage of RNA sequences encoding protein complex components.

Specific ribozyme cleavage sites within any potential RNA target are initially identified by scanning the target molecule for ribozyme cleavage sites which include the following sequences, GUA, GUU and GUC. Once identified, short RNA sequences of between 15 and 20 ribonucleotides corresponding to the region of the target gene containing the cleavage site may be evaluated for predicted structural features, such as secondary structure, that may render the oligonucleotide sequence unsuitable. The suitability of candidate targets may also be evaluated by testing their accessibility to hybridization with complementary oligonucleotides, using ribonuclease protection assays. See, Draper PCT WO 93/23569.

Both anti-sense RNA and DNA molecules and ribozymes of the invention may be prepared by any method known in the art for the synthesis of RNA molecules. See, Draper, id. hereby incorporated in pertinent part by reference herein. These include techniques for chemically synthesizing oligodeoxyribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Various modifications to the DNA molecules may be introduced as a means of increasing intracellular stability and half-life. Possible modifications include but are not limited to the addition of flanking sequences of ribo- or deoxy-nucleotides to the 5' and/or 3' ends of the molecule or the use of phosphorothioate or 2' O-methyl rather than phosphodiesterase linkages within the oligodeoxyribonucleotide backbone.

Therapeutics

Peptide 35, AV3 (SEQ ID NO: 3), FAT and/or FAK or genetic sequences will also be useful in therapy. In one preferred embodiment, an expression vector comprising the SEQ ID NO: 1 coding sequence is inserted into cells, the cells are grown in vitro and then infused in large numbers into patients. The vector may involve the use of an adenovirus comprising cDNA of SEQ ID NO: 1, SEQ ID NO: 3 targeted to a tumor. Target cell populations (e.g., hematopoietic or nerve cells) may be modified by introducing altered forms of peptide 35, AV3 (SEQ ID NO: 3), FAT- and/or FAK-binding molecules in order to modulate the activity of such cells. For example, by reducing or inhibiting a nerve cell within target cells, an abnormal response leading to a condition may be decreased, inhibited, or reversed. Deletion or missense mutants of peptide 35, AV3 (SEQ ID NO: 3), FAT- and/or FAK-binding molecules, that retain the ability to interact with other components of the nervous system but cannot participate in normal function may be used to inhibit an abnormal, deleterious response.

Expression vectors derived from viruses such as retroviruses, vaccinia virus, adenovirus, adeno-associated virus, herpes viruses, several RNA viruses, or bovine papilloma virus, may be used for delivery of nucleotide sequences (e.g., cDNA) encoding recombinant peptide 35 (SEQ ID NO: 1) into the targeted cell population (e.g., tumor cells). Methods which are well known to those skilled in the art can be used to construct recombinant viral vectors containing coding sequences. See, for example, the techniques described in Maniatis et al., Molecular Cloning: A Laboratory Manual, Cold Spring Harbor Laboratory, N.Y. (1989), and in Ausubel et al., Current Protocols in Molecular Biology, Greene Publishing Associates and Wiley Interscience, N.Y. (1989). Alternatively, recombinant nucleic acid molecules encoding protein sequences can be used as naked DNA or in reconstituted system e.g., liposomes or other lipid systems for delivery to target cells (See e.g., Felgner et al., *Nature* 337:387-8, 1989). Several other methods for the direct transfer of plasmid DNA into cells exist for use in human gene therapy and involve targeting the DNA to receptors on cells by complexing the plasmid DNA to proteins. See, Miller, supra.

In its simplest form, gene transfer can be performed by simply injecting minute amounts of DNA into the nucleus of a cell, through a process of microinjection. Capecchi M R, *Cell* 22:479-88 (1980). Once recombinant genes are introduced into a cell, they can be recognized by the cells normal mechanisms for transcription and translation, and a gene product will be expressed. Other methods have also been attempted for introducing DNA into larger numbers of cells. These methods include: transfection, wherein DNA is precipitated with $CaPO_4$ and taken into cells by pinocytosis (Chen C. and Okayama H, *Mol. Cell. Biol.* 7:2745-52 (1987)); electroporation, wherein cells are exposed to large voltage pulses to introduce holes into the membrane (Chu G. et al., *Nucleic Acids Res.*, 15:1311-26 (1987)); lipofection/liposome fusion, wherein DNA is packaged into lipophilic vesicles which fuse with a target cell (Felgner P L., et al., *Proc. Natl. Acad. Sci. USA*. 84:7413-7 (1987)); and particle bombardment using DNA bound to small projectiles (Yang N S. et al., *Proc. Natl. Acad. Sci.* 87:9568-72 (1990)). Another method for introducing DNA into cells is to couple the DNA to chemically modified proteins.

It has also been shown that adenovirus proteins are capable of destabilizing endosomes and enhancing the uptake of DNA into cells. The admixture of adenovirus to solutions containing DNA complexes, or the binding of DNA to polylysine covalently attached to adenovirus using protein crosslinking agents substantially improves the uptake and expression of the recombinant gene. Curiel D T et al., *Am. J. Respir.*, 6:247-52 (1992).

As used herein "gene transfer" means the process of introducing a foreign nucleic acid molecule into a cell. Gene transfer is commonly performed to enable the expression of a particular product encoded by the gene. The product may include a protein, polypeptide, anti-sense DNA or RNA, or enzymatically active RNA. Gene transfer can be performed in cultured cells or by direct administration into animals. Generally gene transfer involves the process of nucleic acid contact with a target cell by non-specific or receptor mediated interactions, uptake of nucleic acid into the cell through the membrane or by endocytosis, and release of nucleic acid into the cytoplasm from the plasma membrane or endosome. Expression may require, in addition, movement of the nucleic acid into the nucleus of the cell and binding to appropriate nuclear factors for transcription.

As used herein "gene therapy" is a form of gene transfer and is included within the definition of gene transfer as used herein and specifically refers to gene transfer to express a therapeutic product from a cell in vivo or in vitro. Gene transfer can be performed ex vivo on cells which are then transplanted into a patient, or can be performed by direct administration of the nucleic acid or nucleic acid-protein complex into the patient.

In another preferred embodiment, a vector having nucleic acid sequences encoding peptide 35 (SEQ ID NO: 1) and AV3 (SEQ ID NO: 3) are provided in which the nucleic acid sequence is expressed only in specific tissue. Methods of achieving tissue-specific gene expression as set forth in International Publication No. WO 93/09236, filed Nov. 3, 1992 and published May 13, 1993.

In all of the preceding vectors set forth above, a further aspect of the invention is that the nucleic acid sequence contained in the vector may include additions, deletions or modifications to some or all of the sequence of the nucleic acid, as defined above.

In another preferred embodiment, a method of gene replacement is set forth. "Gene replacement" as used herein means supplying a nucleic acid sequence which is capable of being expressed in vivo in an animal and thereby providing or augmenting the function of an endogenous gene which is missing or defective in the animal.

Pharmaceutical Formulations and Modes of Administration

The particular compound, antibody, antisense or ribozyme molecule that affects the protein complexes and the disorder of interest, e.g., cancer, can be administered to a patient either by themselves, or in pharmaceutical compositions where it is mixed with suitable carriers or excipient(s). In treating a patient exhibiting a disorder of interest, a therapeutically effective amount of a agent or agents such as these is administered. A therapeutically effective dose refers to that amount of the compound that results in amelioration of symptoms or a prolongation of survival in a patient.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population).

The dose ratio between toxic and therapeutic effects is the therapeutic index and it can be expressed as the ratio $LD_{50}/ED_{50}$. Compounds which exhibit large therapeutic indices are preferred. The data obtained from these cell culture assays and animal studies can be used in formulating a range of dosage for use in human. The dosage of such compounds lies preferably within a range of circulating concentrations that include the $ED_{50}$ with little or no toxicity. The dosage may vary within this range depending upon the dosage form employed and the route of administration utilized.

For any compound used in the method of the invention, the therapeutically effective dose can be estimated initially from cell culture assays. For example, a dose can be formulated in animal models to achieve a circulating plasma concentration range that includes the $IC_{50}$ as determined in cell culture (i.e., the concentration of the test compound which achieves a half-maximal disruption of the protein complex, or a half-maximal inhibition of the cellular level and/or activity of a complex component). Such information can be used to more accurately determine useful doses in humans. Levels in plasma may be measured, for example, by HPLC.

The exact formulation, route of administration and dosage can be chosen by the individual physician in view of the patient's condition. (See e.g. Fingl et al., in The Pharmacological Basis of Therapeutics, 1975, Ch. 1 p. 1). It should be noted that the attending physician would know how to and when to terminate, interrupt, or adjust administration due to toxicity, or to organ dysfunctions. Conversely, the attending physician would also know to adjust treatment to higher levels if the clinical response were not adequate (precluding toxicity). The magnitude of an administrated dose in the management of the oncogenic disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Depending on the specific conditions being treated, such agents may be formulated and administered systemically or locally. Techniques for formulation and administration may be found in Remington's Pharmaceutical Sciences, 18$^{th}$ ed., Mack Publishing Co., Easton, Pa. (1990). Suitable routes may include oral, rectal, transdermal, vaginal, transmucosal, or intestinal administration; parenteral delivery, including intramuscular, subcutaneous, intramedullary injections, as well as intrathecal, direct intraventricular, intravenous, intraperitoneal, intranasal, or intraocular injections, just to name a few.

For injection, the agents of the invention may be formulated in aqueous solutions, preferably in physiologically compatible buffers such as Hanks's solution, Ringer's solution, or physiological saline buffer. For such transmucosal administration, penetrants appropriate to the barrier to be permeated are used in the formulation. Such penetrants are generally known in the art.

Use of pharmaceutically acceptable carriers to formulate the compounds herein disclosed for the practice of the invention into dosages suitable for systemic administration is within the scope of the invention. With proper choice of carrier and suitable manufacturing practice, the compositions of the present invention, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the invention to be formulated as tablets, pills, capsules, liquids, gels, syrups, slurries, suspensions and the like, for oral ingestion by a patient to be treated.

Agents intended to be administered intracellularly may be administered using techniques well known to those of ordinary skill in the art. For example, such agents may be encapsulated into liposomes, then administered as described above. Liposomes are spherical lipid bilayers with aqueous interiors. All molecules present in an aqueous solution at the time of liposome formation are incorporated into the aqueous interior. The liposomal contents are both protected from the external microenvironment and, because liposomes fuse with cell membranes, are efficiently delivered into the cell cytoplasm. Additionally, due to their hydrophobicity, small organic molecules may be directly administered intracellularly.

Pharmaceutical compositions suitable for use in the present invention include compositions wherein the active ingredients are contained in an effective amount to achieve its intended purpose. Determination of the effective amounts is well within the capability of those skilled in the art, especially in light of the detailed disclosure provided herein. In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions. The pharmaceutical compositions of the present invention may be manufactured in a manner that is itself known, e.g., by means of conventional mixing, dissolving, granulating, dragee-making, levitating, emulsifying, encapsulating, entrapping or lyophilizing processes.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxy-methylcellulose, and/or polyvinyl pyrrolidone (PVP). If desired, disintegrating agents may be added, such as the cross-linked polyvinyl pyrrolidone, agar, or alginic acid or a salt thereof such as sodium alginate.

Dragee cores are provided with suitable coating. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Some methods of delivery that may be used include: a. encapsulation in liposomes; b. transduction by retroviral vectors; c. localization to nuclear compartment utilizing nuclear targeting site found on most nuclear proteins; d. transfection of cells ex vivo with subsequent re-implantation or administration of the transfected cells, e. a DNA transporter system.

A peptide 35 and/or AV3 nucleic acid sequence may be administered utilizing an ex vivo approach whereby cells are removed from an animal, transduced with the peptide 35 and/or AV3 nucleic acid sequence and reimplanted into the animal. The liver can be accessed by an ex vivo approach by removing hepatocytes from an animal, transducing the hepatocytes in vitro with the peptide 35 (SEQ ID NO: 1) encoding nucleic acid sequence and reimplanting them into the animal (e.g., as described for rabbits by Chowdhury et al., *Science* 254: 1802-1805, 1991, or in humans by Wilson, *Hum. Gene Ther.* 3: 179-222, 1992) incorporated herein by reference.

Many nonviral techniques for the delivery of a peptide 35 nucleic acid sequence into a cell can be used, including direct naked DNA uptake (e.g., Wolff et al., *Science* 247: 1465-1468, 1990), receptor-mediated DNA uptake, e.g., using DNA coupled to asialoorosomucoid which is taken up by the asialoglycoprotein receptor in the liver (Wu and Wu, *J. Biol. Chem.* 262: 4429-4432, 1987; Wu et al., *J. Biol. Chem.* 266: 14338-14342, 1991), and liposome-mediated delivery (e.g., Kaneda et al., *Expt. Cell Res.* 173: 56-69, 1987; Kaneda et al., *Science* 243: 375-378, 1989; Zhu et al., *Science* 261: 209-211, 1993). Many of these physical methods can be combined with one another and with viral techniques; enhancement of receptor-mediated DNA uptake can be effected, for example, by combining its use with adenovirus (Curiel et al., *Proc. Natl. Acad. Sci. USA* 88: 8850-8854, 1991; Cristiano et al., *Proc. Natl. Acad. Sci. USA* 90: 2122-2126, 1993).

The peptide 35 (SEQ ID NO: 1), AV3 (SEQ ID NO: 3) or nucleic acid encoding peptide 35 (SEQ ID NO: 1), AV3 (SEQ ID NO: 3) may also be administered via an implanted device that provides a support for growing cells. Thus, the cells may remain in the implanted device and still provide the useful and therapeutic agents of the present invention.

Identification of Agents

The complexes, components of such complexes, functional equivalents thereof, and/or cell lines that express such components and exhibit such protein complexes may be used to screen for additional compounds, antibodies, or other molecules capable of modulating the signal transduction event such complexes are involved in. Methods for purifying and/or producing such complexes, components of the complexes, functional equivalents thereof, and/or cell lines are described herein. The compounds, antibodies, or other molecules identified may, for example, act to induce apoptosis in the tumor cell or may modulate the cellular level and/or activity of one or more of the components of such complexes that may modulate, for example, apoptosis.

Such compounds may include, but are not limited to, peptides made of D- and/or L-configuration amino acids (m, for example, the form of random peptide libraries; see Lam et al., *Nature* 354:82-84, 1991), phosphopeptides (m, for example, the form of random or partially degenerate, directed phosphopeptide libraries, see Songyang et al., *Cell* 767-778, 1993), antibodies, and small organic or inorganic molecules. Synthetic compounds, natural products, and other sources of potentially biologically active materials may be screened in a variety of ways, as described herein. The compounds, antibodies, or other molecules identified may be used as oncogenic disorder treatments, as described herein.

Compounds that bind to individual components, or functional portions of the individual components of the complexes (and may additionally be capable of disrupting complex formation) may be identified.

One such method included within the scope of the invention is a method for identifying an agent to be tested for an ability to modulate a signal transduction pathway disorder. The method involves exposing at least one agent to a protein comprising a functional portion of a member of the protein complex for a time sufficient to allow binding of the agent to the functional portion of the member; removing non-bound agents; and determining the presence of the compound bound to the functional portion of the member of the protein complex, thereby identifying an agent to be tested for an ability to modulate a disorder involving a polypeptide complex.

By "signal transduction disorder" is meant any disease or condition associated with an abnormality in a signal transduction pathway. The protein complex referred to is a physical association of a FAT domain and peptide 35, or AV3. The level of interaction between the two components of the complex may be abnormal and thus cause the abnormality in the signal transduction pathway. Alternatively, the level of interaction between the complex components may be normal, but affecting that interaction may effectively treat a signal transduction pathway disorder.

The term "protein" refers to a compound formed of 5-50 or more amino acids joined together by peptide bonds. An "amino acid" is a subunit that is polymerized to form proteins and there are twenty amino acids that are universally found in proteins. The general formula for an amino acid is $H_2N$—CHR—COOH, in which the R group can be anything from a hydrogen atom (as in the amino acid glycine) to a complex ring (as in the amino acid tryptophan).

A functional portion of an individual component of the complexes may be defined here as a protein portion of an individual component of a complex still capable of forming a stable complex with another member of the complex under standard cellular and physiological conditions. For example, a functional portion of a component may include, but is not limited to, a protein portion of FAK which is still capable of stably binding peptide 35, AV3. Further, in the case of the catalytic domains of the individual components of the invention, a functional portion of a catalytic domain may refer to a protein still capable of stably binding a substrate molecule under standard physiological conditions.

One method utilizing this approach that may be pursued in the isolation of such complex component-binding molecules would include the attachment of a component molecule, or a functional portion thereof, to a solid matrix, such as agarose or plastic beads, microtiter wells, petri dishes, or membranes composed of, for example, nylon or nitrocellulose, and the subsequent incubation of the attached component molecule in the presence of a potential component-binding compound or compounds. Attachment to the solid support may be direct or by means of a component specific antibody bound directly to the solid support. After incubation, unbound compounds are washed away, component-bound compounds are recovered.

By utilizing this procedure, large numbers of types of molecules may be simultaneously screened for complex component-binding activity.

The complex components which may be utilized in the above screening method may include, but are not limited to, molecules or functional portions thereof, such as catalytic domains, phosphorylation domains, extracellular domains, or portions of extracellular domains, such as ligand-binding domains, and adaptor proteins, or functional portions thereof. The peptides used may be phosphorylated, e.g., may contain at least one phosphorylated amino acid residue, preferably a phosphorylated Tyr amino acid residue, or may be unphosphorylated. A phosphorylation domain may be defined as a peptide region that is specifically phosphorylated at certain amino acid residues. A functional portion of such a phosphorylation domain may be defined as a peptide capable of being specifically phosphorylated at certain amino acids by a specific protein.

Molecules exhibiting binding activity may be further screened for an ability to disrupt protein complexes. Alternatively, molecules may be directly screened for an ability to promote the complexes. For example, in vitro complex formation may be assayed by, first, immobilizing one component, or a functional portion thereof, of the complex of interest to a solid support. Second, the immobilized complex component may be exposed to a compound such as one identified as above, and to the second component, or a functional portion thereof, of the complex of interest. Third, it may be determined whether or not the second component is still capable of forming a complex with the immobilized component in the presence of the compound. In addition, one could look for an increase in binding.

Additionally, complex formation in a whole cell may be assayed by utilizing co-immunoprecipitation techniques well known to those of skill in the art. Briefly, a cell line capable of forming a complex of interest may be exposed to a compound such as one identified as above, and a cell lysate may be prepared from this exposed cell line. An antibody raised against one of the components of the complex of interest may be added to the cell lysate, and subjected to standard immunoprecipitation techniques. In cases where a complex is still formed, the immunoprecipitation will precipitate the complex, whereas in cases where the complex has been disrupted, only the complex component to which the antibody is raised will be precipitated.

A preferred method for assessing modulation of complex formation within a cell utilizes a method similar to that described above. Briefly, a cell line capable of forming a complex of interest is exposed to a test compound. The cells are lysed and the lysate contacted with an antibody specific to one component of the complex, said antibody having been previously bound to a solid support. Unbound material is washed away, and the bound material is exposed to a second antibody, said second antibody binding specifically to a second component of the complex. The amount of second antibody bound is easily detected by techniques well known in the art. Cells exposed to an inhibitory test compound will have formed a lesser amount of complex compared to cells not exposed to the test compound, as measured by the amount of second antibody bound. Cells exposed to a test compound that promotes complex formation will have an increased amount of second antibody bound.

Agents capable of reducing or inhibiting tumor growth, which involve the formation of for example peptide 35 (SEQ ID NO: 1), AV3 (SEQ ID NO: 3) mediated apoptosis of a tumor cell, may be used in the treatment of patients exhibiting or at risk for such disorders. A sufficient amount of agent or agents such as those described above may be administered to a patient so that the symptoms of the disease or condition are reduced or eliminated.

Purification and Production of Complexes

Described in this Section are methods for the synthesis or recombinant expression of components, or fragments thereof, of the protein complexes of the invention. Also described herein are methods by which cells exhibiting the protein complexes of the invention may be engineered.

The complexes or peptides of the invention may be substantially purified, i.e., may be purified away from at least 90% (on a weight basis), and from at least 99%, if desired, of other proteins, glycoproteins, and other macromolecules with which it is associated. Such purification can be achieved by utilizing a variety of procedures well known to those of skill in the art, such as subjecting cells, tissue or fluid containing the complex to a combination of standard methods, for example, ammonium sulfate precipitation, molecular sieve chromatography, and/or ion exchange chromatography.

Alternatively, or additionally, a peptide or complex may be purified by immunoaffinity chromatography using an immunoabsorbent column to which an antibody is immobilized which is capable of binding to one or more components of the complex. Such an antibody may be monoclonal or polyclonal in origin. Other useful types of affinity purification for the protein complex may utilize, for example, a solid-phase substrate which binds the catalytic kinase domain of a protein, or an immobilized binding site for noncatalytic domains of the components of the complex, which bind in such a manner as to not disrupt the complex. The complex of the present invention may be biochemically purified from a variety of cell or tissue sources.

Methods for the synthesis of polypeptides or fragments thereof, which are capable of acting as components of the complexes of the present invention, are well-known to those of ordinary skill in the art. See, for example, Creighton, Proteins: Structures and Molecular Principles, W. H. Freeman and Co., N.Y. (1983), which is incorporated herein, by reference, in pertinent part.

Components of a complex which have been separately synthesized or recombinantly produced, may be reconstituted to form a complex by standard biochemical techniques well known to those skilled in the art. For example, samples containing the components of the complex may be combined in a solution buffered with greater than about 150 mM NaCl, at a physiological pH in the range of 7, at room temperature. For example, a buffer comprising 20 mM Tris-HCl, pH 7.4, 137 mM NaCl, 10% glycerol, 1% Triton X-100, 0.1% SDS, 0.5% deoxycholate and 2 mM EDTA could be used.

Methods for preparing the components of complexes of the invention by expressing nucleic acid encoding proteins are described herein. Methods which are well known to those skilled in the art can be used to construct expression vectors containing protein coding sequences and appropriate transcriptional and translational control signals. These methods include, for example, in vitro recombinant DNA techniques, synthetic techniques and in vivo recombination/genetic recombination. DNA and RNA synthesis may, additionally, be performed using an automated synthesizers. See, for example, the techniques described in Maniatis et al., Molecular Cloning: A Laboratory Manual, Cold Spring Harbor Laboratory, N.Y. (1989), and in Ausubel et al., Current Protocols in Molecular Biology, Greene Publishing Associates and Wiley Interscience, N.Y. (1989).

A variety of host-expression vector systems may be utilized to express the coding sequences of the components of the complexes of the invention. Such host-expression systems represent vehicles by which the coding sequences of interest may be produced, but also represent cells which may, when transformed or transfected with the appropriate nucleotide coding sequences, exhibit the protein complexes of the invention. These include but are not limited to microorganisms such as bacteria (e.g., *E. coli, B. subtilis*) transformed with recombinant bacteriophage DNA, plasmid DNA or cosmid DNA expression vectors containing protein coding sequences; yeast (e.g., *Saccharomyces* and *Pichia*) transformed with recombinant yeast expression vectors containing the protein coding sequencers; insect cell systems infected with recombinant virus expression vectors (e.g., baculovirus) containing the protein coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the protein coding sequences coding sequence; or mammalian cell systems (e.g., COS, CHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5K promoter)

In bacterial systems a number of expression vectors may be advantageously selected depending upon the use intended for the complex being expressed. For example, when large quantities of complex proteins are to be produced for the generation of antibodies or to screen peptide libraries, vectors which direct the expression of high levels of fusion protein products that are readily purified may be desirable. Such vectors include but are not limited to the *E. coli* expression vector pUR278 (Ruther et al., EMBO J. 2:1791, 1983), in which the protein coding sequence may be ligated individually into the vector in frame with the lac Z coding region so that a fusion protein is produced; pIN vectors (Inouye and Inouye, *Nucleic acids Res.* 13:3101-3109, 1985; Van Heeke & Schuster, *J. Biol. Chem.* 264:5503-5509, 1989); and the like. pGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The PGEX vectors are designed to include thrombin or factor Xa protease cleavage sites so that the cloned protein can be released from the GST moiety.

In an insect system, *Autographa californica* nuclear polyhedrosis virus (AcNPV) is used as a vector to express foreign genes. The virus grows in *Spodoptera frugiperda* cells. The peptide coding sequence may be cloned individually into non-essential regions (for example the polyhedrin gene) of the virus and placed under control of an AcNPV promoter (for example the polyhedrin promoter). Successful insertion of the peptide 35 (SEQ ID NO: 1), AV3 (SEQ ID NO: 3) coding sequence will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed (e.g., see Smith et al., *J. Biol.* 46:584, 1983; Smith, U.S. Pat. No. 4,215,051).

In mammalian host cells, a number of viral based expression systems may be utilized. In cases where an adenovirus is used as an expression vector, the peptide coding sequence may be ligated to an adenovirus transcription/translation control peptide, e.g., the late promoter and tripartite leader sequence. This chimeric gene may then be inserted in the adenovirus genome by in vitro or in vivo recombination. Insertion into a non-essential region of the viral genome (e.g., region E1 or E3) will result in a recombinant virus that is viable and capable of expressing proteins in infected hosts. (E.g., See Logan & Shenk, *Proc. Natl. Acad. Sci. USA* 81:3655-3659, 1984). Specific initiation signals may also be required for efficient translation of inserted coding sequences. These signals include the ATG initiation codon and adjacent sequences.

In cases where an entire protein gene, including its own initiation codon and adjacent sequences, is inserted into the appropriate expression vector, no additional translational control signals may be needed. However, in cases where only a portion of the coding sequence is inserted, exogenous translational control signals, including the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., *Methods in Enzymol.* 153:516-544, 1987)

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins. Appropriate cells lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERO, BHK, HeLa, COS, MDCK, 293, 3T3, WI38, etc.

For long-term, high-yield production of recombinant proteins, stable expression is preferred. For example, cell lines which stably co-express both the proteins may be engineered. Rather than using expression vectors which contain viral origins of replication, host cells can be transformed with the protein encoding DNA independently or coordinately controlled by appropriate expression control elements (e.g., promoter, enhancer, sequences, transcription terminators, polyadenylation sites, etc.), and a selectable marker.

Following the introduction of foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express peptide 35, variants, and fragments thereof. Such engineered cell lines are particularly useful in screening and evaluation of compounds that effect signals mediated by the peptides.

A number of selection systems may be used, including but not limited to the Herpes simplex virus thymidine kinase (Wigler et al., *Cell* 11:223, 1977), hypoxanthine-guanine phosphoribosyltransferase (Szybalska & Szybalski, *Proc. Natl. Acad. Sci. USA* 48:2026, 1962), and adenine phosphoribosyltransferase (Lowy et al., *Cell* 22:817, 1980) genes can be employed in tk⁻, hgprt⁻ or aprt⁻ cells, respectively. Also, antimetabolite resistance can be used as the basis of selection for dhfr, which confers resistance to methotrexate (Wigler et al., *Proc. Natl. Acad. Sci. USA* 77:3567, 1980; O'Hare et al., *Proc. Natl. Acad. Sci. USA* 78:1527, 1981); gpt, which confers resistance to mycophenolic acid (Mulligan & Berg, *Proc. Natl. Acad. Sci. USA* 78:2072, 1981); neo, which confers resistance to the aminoglycoside G-418 (Colberre-Garapin et al., *J. Mol. Biol.* 150:1, 1981); and hygro, which confers resistance to hygromycin (Santerre et al. *Gene* 30:147, 1984) genes.

New members of the protein families may be identified and isolated by molecular biological techniques well known in the art. For example, a previously unknown protein encoding gene may be isolated by performing a polymerase chain reaction (PCR) using two degenerate oligonucleotide primer pools designed on the basis of highly conserved sequences within domains common to members of the protein family.

The template for the reaction may be cDNA obtained by reverse transcription of mRNA prepared from cell lines or tissue known to express complexes. The PCR product may be subcloned and sequenced to insure that the amplified sequences represent the sequences of a member of the FAK subfamily. The PCR fragment may then be used to isolate a full length protein cDNA clone by radioactively labeling the amplified fragment and screening a bacteriophage cDNA library. Alternatively, the labeled fragment may be used to screen a genomic library. For a review of cloning strategies which may be used. See e.g., Maniatis, Molecular Cloning: A Laboratory Manual, Cold Springs Harbor Press, N.Y. (1989); and Ausubel et al., Current Protocols in Molecular Biology, Green Publishing Associates and Wiley Interscience, N.Y. (1989). A general method for cloning previously unknown proteins has been described by Skolnik (Skolnik, E. Y., Cell 65:75, 1991) and Skolnik et al., (U.S. patent application Ser. No. 07/643,237) which are incorporated herein, by reference, in their entirety, including drawings.

Derivatives of FAK-Binding Peptides

Also provided herein are functional derivatives of a peptide. By "functional derivative" is meant a "chemical derivative," "fragment," "variant," "chimera," or "hybrid" of the peptide and/or peptide-FAK complex, which terms are defined below. A functional derivative retains at least a portion of the function of the protein, for example reactivity with an antibody specific for the complex, enzymatic activity or binding activity mediated through noncatalytic domains, which permits its utility in accordance with the present invention.

A "chemical derivative" of the complex contains additional chemical moieties not normally a part of the protein. Such moieties may improve the molecule's solubility, absorption, biological half life, and the like. The moieties may alternatively decrease the toxicity of the molecule, eliminate or attenuate any undesirable side effect of the molecule, and the like. Moieties capable of mediating such effects are disclosed in Remington's Pharmaceutical Sciences (1980). Procedures for coupling such moieties to a molecule are well known in the art. Covalent modifications of the protein complex or peptides are included within the scope of this invention. Such modifications may be introduced into the molecule by reacting targeted amino acid residues of the peptide with an organic derivatizing agent that is capable of reacting with selected side chains or terminal residues, as described below.

Cysteinyl residues most commonly are reacted with alpha-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylprocarbonate at pH 5.5-7.0 because this agent is relatively specific for the histidyl side chain. Parabromophenacyl bromide also is useful; the reaction is preferably performed in 0.1M sodium cacodylate at pH 6.0.

Lysinyl and amino terminal residues are reacted with succinic or other carboxylic acid anhydrides. Derivatization with these agents has the effect or reversing the charge of the lysinyl residues. Other suitable reagents for derivatizing primary amine containing residues include imidoesters such as methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine alpha-amino group.

Tyrosyl residues are well-known targets of modification for introduction of spectral labels by reaction with aromatic diazonium compounds or tetranitromethane. Most commonly, N-acetylimidizol and tetranitromethane are used to form O-acetyl tyrosyl species and 3-nitro derivatives, respectively.

Carboxyl side groups (aspartyl or glutamyl) are selectively modified by reaction carbodiimide (R'—N—C—N—R') such as 1-cyclohexyl-3-(2-morpholinyl(4-ethyl)carbodiimide or 1-ethyl-3-(4-azonia-4,4-dimethylpentyl)carbodiimide. Furthermore, aspartyl and glutamyl residue are converted to asparaginyl and glutaminyl residues by reaction with ammonium ions.

Glutaminyl and asparaginyl residues are frequently deamidated to the corresponding glutamyl and aspartyl residues. Alternatively, these residues are deamidated under mildly acidic conditions. Either form of these residues falls within the scope of this invention.

Derivatization with bifunctional agents is useful, for example, for cross-linking the component peptides of the complexes to each other or the complex to a water-insoluble support matrix or to other macromolecular carriers. Commonly used cross-linking agents include, for example, 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), and bifunctional maleimides such as bis-N-maleimido-1,8-octane. Derivatizing agents such as methyl-3->p-azidophenyl)dithiolpropioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

Other modifications include hydroxylation of proline and lysine, phosphorylation of hydroxyl groups of seryl or threonyl residues, methylation of the alpha-amino groups of lysine, arginine, and histidine side chains (Creighton, T. E., Proteins: Structure and Molecular Properties, W. H. Freeman & Co., San Francisco, pp. 79-86 (1983)), acetylation of the N-terminal amine, and, in some instances, amidation of the C-terminal carboxyl groups.

Such derivatized moieties may improve the stability, solubility, absorption, biological half life, and the like. The moieties may alternatively eliminate or attenuate any undesirable side effect of the protein complex and the like. Moieties capable of mediating such effects are disclosed, for example, in Remington's Pharmaceutical Sciences, 18th ed., Mack Publishing Co., Easton, Pa. (1990).

The term "fragment" is used to indicate a polypeptide derived from the amino acid sequence of the proteins, of the complexes having a length less than the full-length polypeptide from which it has been derived. Such a fragment may, for example, be produced by proteolytic cleavage of the full-length protein. Preferably, the fragment is obtained recombinantly by appropriately modifying the DNA sequence encoding the proteins to delete one or more amino acids at one or more sites of the C-terminus, N-terminus, and/or within the native sequence. Fragments of a protein, when present in a complex resembling the naturally occurring complex, are useful for screening for compounds that act to modulate signal transduction leading to induction of apoptosis and/or motility and/or invasion. It is understood that such fragments, when present in a complex may retain one or more characterizing portions of the native complex. Examples of such retained characteristics include: catalytic activity; substrate specificity; interaction with other molecules in the intact cell; regulatory functions; or binding with an antibody specific for the native complex, or an epitope thereof.

Another functional derivative intended to be within the scope of the present invention is a complex comprising at least one "variant" polypeptide which either lack one or more amino acids or contain additional or substituted amino acids relative to the native polypeptide. The variant may be derived from a naturally occurring complex component by appropriately modifying the protein DNA coding sequence to add, remove, and/or to modify codons for one or more amino acids at one or more sites of the C-terminus, N-terminus, and/or within the native sequence. It is understood that such variants having added, substituted and/or additional amino acids retain one or more characterizing portions of the native complex, as described above.

A functional derivative of complexes comprising proteins with deleted, inserted and/or substituted amino acid residues may be prepared using standard techniques well-known to those of ordinary skill in the art. For example, the modified components of the functional derivatives may be produced using site-directed mutagenesis techniques (as exemplified by Adelman et al., 1983, DNA 2:183) wherein nucleotides in the DNA coding the sequence are modified such that a modified coding sequence is modified, and thereafter expressing this recombinant DNA in a prokaryotic or eukaryotic host cell, using techniques such as those described infra.

Alternatively, components of functional derivatives of complexes with amino acid deletions, insertions and/or substitutions may be conveniently prepared by direct chemical synthesis, using methods well-known in the art. The functional derivatives of the complexes typically exhibit the same qualitative biological activity as the native complexes.

Evaluation of Disorders

The protein complexes of the invention involved in disorders may be utilized in developing a prognostic evaluation of the condition of a patient suspected of exhibiting such a disorder. For example, biological samples obtained from patients suspected of exhibiting a disorder involving a protein complex may be assayed for the presence of such complexes.

If such a protein complex is normally present, and the development of the disorder is caused by an abnormal quantity of the complex, the assay should compare complex levels in the biological sample to the range expected in normal tissue of the same cell type.

Among the assays which may be undertaken may include, but are not limited to isolation of the protein complex of interest from the biological sample, or assaying for the presence of the complex by exposing the sample to an antibody specific for the complex, but non-reactive to any single, non-complexed component, and detecting whether antibody has specifically bound.

Alternatively, one or more of the components of the protein complex may be present in an abnormal level or in a modified form, relative to the level or form expected is normal, nononcogenic tissue of the same cell type. It is possible that overexpression of both components may indicate a particularly aggressive disorder. Thus, an assessment of the individual and levels of mRNA and protein in diseased tissue cells may provide valuable clues as to the course of action to be undertaken in treatment of such a disorder. Assays of this type are well known to those of skill in the art, and may include, but are not limited to, Northern blot analysis, RNAse protection assays, and PCR for determining mRNA levels. Assays determining protein levels are also well known to those of skill in the art, and may include, but are not limited to, Western blot analysis, immunoprecipitation, and ELISA analysis. Each of these techniques may also reveal potential differences in the form (e.g., the primary, secondary, or tertiary amino acid sequence, and/or post-translational modifications of the sequence) of the component(s).

Chimeric Molecules

The peptides or other molecules that specifically bind FAK or FAT of the invention can be conjugated to a second molecule to form a chimeric molecule. The second molecule can be any molecule that can be conjugated to the molecule that specifically binds FAK or FAT. For example, the second molecule can be a detectable label, a targeting ligand, or a delivery vehicle.

The molecule that specifically binds FAK or FAT can be conjugated with one or more detectable labels can be used to detect a receptor or ligand to which the molecule binds, e.g., in the in situ localization of FAK in cancer cells. Detectable labels for use in the invention can be any substance that can be conjugated to the molecule that specifically binds FAK. Suitable detectable labels are those that can be detected, for example, by spectroscopic, photochemical, biochemical, immunochemical, electrical, optical or chemical means. Useful detectable labels in the present invention include biotin or streptavidin, fluorescent dyes (e.g., fluorescein isothiocyanate [FITC], Texas red, rhodamine, green fluorescent protein, and the like), radiolabels (e.g., $^3$H, $^{125}$I, $^{35}$S, $^{14}$C, $^{32}$P, $^{111}$In, $^{97}$Ru, $^{67}$Ga, $^{68}$Ga, or $^{72}$As,), radio-opaque substances such as metals for radioimaging, paramagnetic agents for magnetic resonance imaging, enzymes (e.g., horseradish peroxidase, alkaline phosphatase and others commonly used in an ELISA), light-emitting nanoparticles, and calorimetric labels such as colloidal gold or colored glass or plastic (e.g. polystyrene, polypropylene, latex, etc.) beads.

Means of detecting such labels are well known to those of skill in the art. Thus, for example, radiolabels may be detected using photographic film or scintillation counters, fluorescent markers may be detected using a photo detector to detect emitted illumination. Enzymatic labels are typically detected by providing the enzyme with a substrate and detecting the reaction product produced by the action of the enzyme on the substrate, and colorimetric labels are detected by simply visualizing the colored label, and so forth.

FAK-binding molecules conjugated with one or more targeting ligands (i.e., molecules that can bind a particular receptor) can be used to mediate binding to a particular receptor or cell expressing the receptor. Examples of such targeting ligands include antibodies (or the antigen-binding portion of antibodies); and chemokines, growth factors, soluble cytokine receptors (e.g., those lacking a transmembrane domain), superantigens, or other molecules that bind a particular receptor.

A FAK-binding molecule conjugated to a one or more delivery vehicles is also within the invention. A preferred example of a delivery vehicle is an agent that allows the chimeric molecule to penetrate a lipid bilayer or cell membrane. For instance, as described below, an FAK-binding peptide is conjugated to a TAT peptide (See, e.g., Nagahara H et al., Nature Med 4:1449-1452, 1998; Gius D R et al., Cancer Res 59:2577-2580, 1999). Other agents that might be used include the antennapedia (ANT) homeodomain in Drosophila or polyethylene glycol.

Second molecules can be conjugated (e.g., covalently bonded) to a FAK-binding molecule by any method known in the art for conjugating two such molecules together. For example, the FAK-binding molecule can be chemically derivatized with an second molecule either directly or using a linker (spacer). Several methods and reagents (e.g., cross-linkers) for mediating this conjugation are known. See, e.g., catalog of Pierce Chemical Company; and Means and Feeney, *Chemical Modification of Proteins*, Holden-Day Inc., San Francisco, Calif. 1971. Various procedures and linker molecules for attaching various compounds are described, for example, in European Patent Application No. 188,256; U.S. Pat. Nos. 4,671,958; 4,659,839; 4,414,148; 4,699,784; 4,680,338; 4,569,789; and 4,589,071; and Borlinghaus et al. *Cancer Res.* 47: 4071-4075 (1987).

Where the second molecule is a peptide, the chimeric molecule including the FAK-binding molecule and the second molecule can be a fusion protein. Fusion proteins can be prepared using conventional techniques in molecular biology to join the two genes in frame into a single nucleic acid, and then expressing the nucleic acid in an appropriate host cell under conditions in which the fusion protein is produced. A FAK-binding molecule may be conjugated to one or more second molecule(s) in various orientations. For example, the second molecule may be joined to either the amino or carboxy termini of the FAK-binding molecule.

In some circumstances, it is desirable to free the second molecule from the FAK-binding molecule when the chimeric molecule has reached its target site. Therefore, chimeric conjugates comprising linkages that are cleavable in the vicinity of the target site may be used when the second is to be released at the target site. Cleaving of the linkage to release the second molecule from the FAK-binding molecule may be prompted by enzymatic activity or conditions to which the conjugate is subjected either inside the target cell or in the vicinity of the target site. When the target site is within a cell, a linker which is cleavable under conditions present at the intracellular site may be used.

In another preferred embodiment, the invention provides administering a chimeric fusion molecule with a cocktail of one or more compounds such as for example, endostatin, angiogenin, angiostatin, chemokines, angioarrestin, angiostatin (plasminogen fragment), basement-membrane collagen-derived anti-angiogenic factors (tumstatin, canstatin, or arrestin), anti-angiogenic antithrombin III, cartilage-derived inhibitor (CDI), CD59 complement fragment, fibronectin fragment, gro-beta, heparinases, heparin hexasaccharide fragment, human chorionic gonadotropin (hCG), interferon alpha/beta/gamma, interferon inducible protein (IP-10), interleukin-12, kringle 5 (plasminogen fragment), metalloproteinase inhibitors (TIMPs), 2-methoxyestradiol, placental ribonuclease inhibitor, plasminogen activator inhibitor, platelet factor-4 (PF4), prolactin 16 kD fragment, proliferin-related protein (PRP), various retinoids, tetrahydrocortisol-S, thrombospondin-1 (TSP-1), transforming growth factor-beta (TGF-b), vasculostatin, vasostatin (calreticulin fragment) and the like.

Cytolytic molecules that can be used to fuse to an FAK-binding molecule, include, but are not limited to TNF-α, TNF-β, suitable effector genes such as those that encode a peptide toxin—such as ricin, abrin, diphtheria, gelonin, *Pseudomonas* exotoxin A, *Crotalus durissus terrificus* toxin, *Crotalus adamenteus* toxin, *Naja naja* toxin, and *Naja mocambique* toxin. (Hughes et al., *Hum. Exp. Toxicol.* 15:443, 1996; Rosenblum et al., *Cancer Immunol. Immunother.* 42:115, 1996; Rodriguez et al., *Prostate* 34:259, 1998; Mauceri et al., *Cancer Res.* 56:4311; 1996).

Also suitable are other peptides that induce or mediate apoptosis—such as the ICE-family of cysteine proteases, the Bcl-2 family of proteins, Bax, bclXs and caspases (Favrot et al., *Gene Ther.* 5:728, 1998; McGill et al., *Front. Biosci.* 2:D353, 1997; McDonnell et al., *Semin. Cancer Biol.* 6:53, 1995). Another potential anti-tumor agent is apoptin, a protein that induces apoptosis even where small drug chemotherapeutics fail (Pietersen et al., *Adv. Exp. Med. Biol* 465: 153, 2000). Koga et al. (*Hu. Gene Ther.* 11:1397, 2000) propose a telomerase-specific gene therapy using the hTERT gene promoter linked to the apoptosis gene Caspase-8 (FLICE).

Also of interest are enzymes present in the lytic package that cytotoxic T lymphocytes or LAK cells deliver to their targets. Perforin, a pore-forming protein, and Fas ligand are major cytolytic molecules in these cells (Brandau et al., *Clin. Cancer Res.* 6:3729, 2000; Cruz et al., *Br. J. Cancer* 81:881, 1999). CTLs also express a family of at least 11 serine proteases termed granzymes, which have four primary substrate specificities (Kam et al., *Biochim. Biophys. Acta* 1477:307, 2000). Low concentrations of streptolysin 0 and pneumolysin facilitate granzyme B-dependent apoptosis (Browne et al., *Mol. Cell. Biol.* 19:8604, 1999).

Other suitable effectors encode polypeptides having activity that is not itself toxic to a cell, but renders the cell sensitive to an otherwise nontoxic compound—either by metabolically altering the cell, or by changing a non-toxic prodrug into a lethal drug. Exemplary is thymidine kinase (tk), such as may be derived from a herpes simplex virus, and catalytically equivalent variants. The HSV tk converts the anti-herpetic agent ganciclovir (GCV) to a toxic product that interferes with DNA replication in proliferating cells.

If desired, although not required, factors may also be included, such as, but not limited to, interleukins, e.g. IL-2, IL-3, IL-6, and IL-11, as well as the other interleukins, the colony stimulating factors, such as GM-CSF, interferons, e.g. γ-interferon, erythropoietin.

In another preferred embodiment, the invention provides for antibody fusion molecules comprising FAK-binding molecules fused to the $F_c$ region, $C_H1$, $C_H2$ and/or $C_H3$, Fab, Fab', $F(ab')_2$, single chain Fv ($S_cFv$) and Fv fragments, as well as any portion of an antibody having specificity toward a desired target epitope or epitopes. Also preferred are antibodies or antibody fragments or to single chain, two-chain, and multi-chain proteins and glycoproteins belonging to the classes of polyclonal, monoclonal, chimeric, bispecific and hetero immunoglobulins (monoclonal antibodies being preferred); it also includes synthetic and genetically engineered variants of these immunoglobuins.

In another preferred embodiment, carrier domains within the invention can be used to introduce other effector functions to the chimeric molecule. For introducing an effector function to the chimeric molecule, the carrier domain can be a protein that has been shown to possess cytotoxic or immune response-stimulating properties. For instance, carrier domains for introducing a cytotoxic function to the chimeric molecule include a bacterial toxin, ricin, abrin, saporin, pokeweed viral protein, and constant region domains from an immunoglobulin molecule (e.g., for antibody dependent cell-mediated cytotoxicity). Chimeric molecules that contain a cytotoxic carrier domain can be used to selectively kill cells.

For introducing immune response-stimulating properties to a chimeric molecule, carrier domains within the invention include any known to activate an immune system component. For example, antibodies and antibody fragments (e.g., $CH_2$—$CH_3$) can be used as a carrier domain to engage Fc receptors or to activate complement components. A number of other immune system-activating molecules are known that might also be used as a carrier domain, e.g., microbial superantigens, adjuvant components, lipopolysaccharide (LPS), and lectins with mitogenic activity. Other carrier domains that can be used to introduce an effector function to the chimeric molecule can be identified using known methods. For instance, a molecule can be screened for suitability as a carrier domain by fusing the molecule to an anti-angiogenic agent and testing the chimeric molecule in in vitro or in vivo cell cytotoxicity and humoral response assays.

Tumor Antigens

In another preferred embodiment, the chimeric fusion molecules comprise a modulatory or cytolytic molecule, as described above, e.g. peptide 35 (SEQ ID NO: 1), AV3 (SEQ ID NO: 3) to an antibody or fragment thereof, specific for tumor antigens. Many tumor antigens are well known in the art. See for example, Van den Eynde B J, van der Bruggen P. *Curr Opin Immunol* 1997; 9: 684-93; Houghton A N, Gold J S, Blachere N E. *Curr Opin Immunol* 2001; 13: 134-140; van der Bruggen P, Zhang Y, Chaux P, Stroobant V, Panichelli C, Schultz E S, Chapiro J, Van den Eynde B J, Brasseur F, Boon T. *Immunol Rev* 2002; 188: 51-64, which are herein incorporated by reference in pertinent part. Alternatively, many antibodies directed towards tumor antigens are commercially available.

Non-limiting examples of tumor antigens, include, tumor antigens resulting from mutations, such as: alpha-actinin-4 (lung carcinoma); BCR-ABL fusion protein (b3a2) (chronic myeloid leukemia); CASP-8 (head and neck squamous cell carcinoma); beta-catenin (melanoma); Cdc27 (melanoma); CDK4 (melanoma); dek-can fusion protein (myeloid leukemia); Elongation factor 2 (lung squamous carcinoa); ETV6-AML1 fusion protein (acute lymphoblastic leukemia); LDLR-fucosyltransferaseAS fusion protein (melanoma); overexpression of HLA-A2$^d$ (renal cell carcinoma); hsp70-2 (renal cell carcinoma); KLAAO205 (bladder tumor); MART2 (melanoma); MUM-1f (melanoma); MUM-2 (melanoma); MUM-3 (melanoma); neo-PAP (melanoma); Myosin class I (melanoma); OS-9g (melanoma); pml-RARalpha fusion protein (promyelocytic leukemia); PTPRK (melanoma); K-ras (pancreatic adenocarcinoma); N-ras (melanoma). Examples of differentiation tumor antigens include, but not limited to: CEA (gut carcinoma); gp100/Pmel17 (melanoma); Kallikrein 4 (prostate); mammaglobin-A (breast cancer); Melan-A/MART-1 (melanoma); PSA (prostate carcinoma); TRP-1/gp75 (melanoma); TRP-2 (melanoma); tyrosinase (melanoma). Over or under-expressed tumor antigens include but are not limited to: CPSF (ubiquitous); EphA3; G250/MN/CAIX (stomach, liver, pancreas); HER-2/neu; Intestinal carboxyl esterase (liver, intestine, kidney); alpha-foetoprotein (liver); M-CSF (liver, kidney); MUC1 (glandular epithelia); p53 (ubiquitous); PRAME (testis, ovary, endometrium, adrenals); PSMA (prostate, CNS, liver); RAGE-1 (retina); RU2AS (testis, kidney, bladder); survivin (ubiquitous); Telomerase (testis, thymus, bone marrow, lymph nodes); WT1 (testis, ovary, bone marrow, spleen); CA125 (ovarian).

Anti-Angiogenic Chimeric Molecules

In another preferred embodiment, the invention provides chimeric molecules that include both an anti-angiogenic agent domain and FAK-binding molecule domain and/or a carrier domain or variation in domains thereof. The anti-angiogenic agent domain reduces tumor growth (e.g., by inhibiting angiogenesis), while the carrier domain confers a functional attribute to the chimeric molecule. For instance, where the carrier domain is an Ig domain, it can function to target the chimeric molecule to a particular site (e.g., the antigen-binding portion of the antibody binds to an antigen expressed by a target cell and/or the Fc portion of the Ig domain can target the chimeric molecule to an Fc receptor-bearing cell); to increase stability of the chimeric molecule (e.g., for in vitro storage or in vivo delivery); to impart an effector function to the chimeric molecule (e.g., immune response-stimulating, cytotoxicity, etc.); or to facilitate purification of the chimeric molecule.

If an anti-angiogenic domain is desired, any substance that exerts an anti-angiogenic effect might be used as the anti-angiogenic agent, e.g., endostatin, anti-angiogenic chemokines, angioarrestin, angiostatin (plasminogen fragment), basement-membrane collagen-derived anti-angiogenic factors (tumstatin, canstatin, or arrestin), anti-angiogenic anti-thrombin III, cartilage-derived inhibitor (CDI), CD59 complement fragment, fibronectin fragment, gro-beta, heparinases, heparin hexasaccharide fragment, human chorionic gonadotropin (hCG), interferon alpha/beta/gamma, interferon inducible protein IP-10), interleukin-12, kringle 5 (plasminogen fragment), metalloproteinase inhibitors (TIMPs), 2-methoxyestradiol, placental ribonuclease inhibitor, plasminogen activator inhibitor, platelet factor-4 (PF4), prolactin 16 kD fragment, proliferin-related protein (PRP), various retinoids, tetrahydrocortisol-S, thrombospondin-1 (TSP-1), transforming growth factor-beta (TGF-b), vasculostatin, vasostatin (calreticulin fragment), and other naturally occurring or man-made inhibitors of neovascularization.

The anti-angiogenic agent can be an intact molecule, a functionally fragment of the agent, or a naturally occurring or man-made mutant of the agent. For example, endostatin domains include any molecule derived from a native endostatin that shares a functional activity of endostatin, e.g., the ability to inhibit VEGF production or new vessel formation The endostatin domain can be a native endostatin or a fragment of a native endostatin that retains a functional activity of a native endostatin. The endostatin domain can also be a non-naturally occurring form a endostatin (e.g., a mutant form created by amino acid substitution) that retains a functional activity of a native endostatin.

The carrier domain can be any substance that imparts a function to the chimeric molecule. For example, a carrier domain can be a molecule that increases the stability of the chimeric molecule (e.g., for in vitro storage or in vivo delivery); introduces an effector function to the chimeric molecule (e.g., immune response-stimulating, cytotoxicity, etc.); or facilitates purification of the chimeric molecule. For increasing the stability of the chimeric molecule, the carrier domain can be a protein that has been shown to stabilize molecules in an in vitro storage or in vivo delivery setting. For example, carrier domains for increasing the stability of the chimeric molecule include one or more domains from an Ig molecule (e.g., a $CH_2$—$CH_3$ fragment). Other carrier domains that can be used to stabilize the chimeric molecule can be identified empirically. For instance, a molecule can be screened for suitability as a carrier domain by conjugating the molecule to anti-angiogenic agent and testing the conjugated product in in vitro or in vivo stability assays.

In another preferred embodiment, carrier domains within the invention facilitate purification of the chimeric molecule. Any molecule known to facilitate purification of a chimeric molecule can be used. Representative examples of such carrier domains include antibody fragments and affinity tags (e.g., GST, HIS, FLAG, and HA). Chimeric molecules containing an affinity tag can be purified using immunoaffinity techniques (e.g., agarose affinity gels, glutathione-agarose beads, antibodies, and nickel column chromatography). Chimeric molecules that contain an Ig domain as a carrier domain can be purified using immunoaffinity chromatography techniques known in the art (e.g., protein A or protein G chromatography).

Other carrier domains within the invention that can be used to purify the chimeric molecule can be readily identified by testing the molecules in a functional assay. For instance, a molecule can be screened for suitability as a carrier domain by fusing the molecule to an anti-angiogenic agent and testing the fusion for purity and yield in an in vitro assay. The purity of recombinant proteins can be estimated by conventional techniques, for example, SDS-PAGE followed by the staining of gels with Coomassie-Blue.

A number of other carrier domains can be used to impart additional effector functions to the chimeric molecule. These include other cytotoxins, drugs, detectable labels, targeting ligands, and delivery vehicles. Examples of these are described in U.S. Pat. No. 6,518,061 and U.S. published patent application number 20020159972.

A preferred carrier domain for use in the chimeric molecule is an Ig or portion of an Ig. The Ig domain might take the form of a single chain antibody (e.g., a scFV), an Fab fragment, an F(ab)$_2$ fragment, an Ig heavy chain, or an Ig in which one or more of the constant regions has been removed. The Ig domain can be derived from any Ig class including IgG, IgM, IgE, IgA, IgD and any subclass thereof. In some applications, it is preferred that the Ig domain includes a large hinge region, e.g., one from IgG3.

In another preferred embodiment, the Ig domain is a minibody. A small protein scaffold called a "minibody" was designed using a part of the Ig VH domain as the template (Pessi et al., 1993). Minibodies with high affinity (dissociation constant ($K_d$) about $10^{-7}$ M) to interleukin-6 were identified by randomizing loops corresponding to CDR1 and CDR2 of VH and then selecting mutants using the phage display method Martin et al., 1994). These experiments demonstrated that the essence of the Ab function could be transferred to a smaller system. Thus, the chimeric fusion molecule may comprise a minibody Ig domain.

Chimeric molecules can be prepared using conventional techniques in molecular biology or protein chemistry. Where the chimeric molecule is a fusion protein, molecular biology methods can be used to join two or more genes in frame into a single nucleic acid. The nucleic acid can then be expressed in an appropriate host cell under conditions in which the chimeric molecule is produced. A carrier domain might also be conjugated (e.g., covalently bonded) to an anti-angiogenic agent domain by other methods known in the art for conjugating two such molecules together. For example, the FAK-binding molecule domain can be chemically derivatized with a carrier domain either directly or using a linker (spacer). Several methods and reagents (e.g., cross-linkers) for mediating this conjugation are known. See, e.g., catalog of Pierce Chemical Company; and Means and Feeney, *Chemical Modification of Proteins*, Holden-Day Inc., San Francisco, Calif. 1971; "Monoclonal Antibody-Toxin Conjugates Aiming the Magic Bullet," Thorpe et al., *Monoclonal Antibodies in Clinical Medicine*, Academic Press, pp. 168-190 (1982); Waldmann (1991) *Science,* 252: 1657; and U.S. Pat. Nos. 4,545, 985 and 4,894,443.

An FAK-binding molecule domain may be fused or conjugated to a carrier domain in various orientations. For example, the carrier domain may be joined to either the amino or carboxy termini of a peptide as identified by SEQ ID NO: 1, SEQ ID NO: 3. The peptide may also be joined to an internal region of the carrier domain, or conversely, the carrier domain may be joined to an internal location of the FAK-binding molecule domain.

In some circumstances, it is desirable to free the carrier domain from the FAK-binding molecule domain when the chimeric molecule has reached its target site. Therefore, chimeric conjugates featuring linkages that are cleavable in the vicinity of the target site may be used when one of the domains is to be released at the target site. Cleaving of the linkage to release the carrier domain from the FAK-binding molecule domain may be prompted by enzymatic activity or conditions to which the conjugate is subjected either inside the target cell or in the vicinity of the target site. When the target site is a tumor, a linker which is cleavable under conditions present at the tumor site (e.g. when exposed to tumor-associated enzymes or acidic pH) may be used. A number of different cleavable linkers are known to those of skill in the art. See, e.g., U.S. Pat. Nos. 4,618,492; 4,542,225; and 4,625, 014. The mechanisms for release of an agent from these linker groups include, for example, irradiation of a photolabile bond and acid-catalyzed hydrolysis. U.S. Pat. No. 4,671,958, for example, includes a description of immunoconjugates comprising linkers which are cleaved at the target site in vivo by the proteolytic enzymes of the patient's complement system. In view of the large number of methods that have been reported for attaching a variety of radiodiagnostic compounds, radiotherapeutic compounds, drugs, toxins, and other agents to proteins one skilled in the art will be able to determine a suitable method for attaching a given carrier domain to an FAK-binding molecule domain.

Bispecific Chimeric Molecules

In another preferred embodiment, chimeric molecules comprising an FAK-binding molecule domain is fused to a bispecific antibody domain or fragments thereof. In one aspect of the invention, the bispecific antibody comprises two monoclonal antibodies. However, the bispecific antibody can comprise two polyclonal antibodies or an engineered bispecific antibody. Preferably, each of the specificities of the bispecific antibody are directed to one or more tumor antigens and/or specific cell or tissue. Antibodies can be raised against any tumor antigen from a patient. Thus the targeting of the chimeric molecule can be individually tailored as the tumor displays different antigens.

Bispecific antibodies may be constructed by hybrid-hybridoma techniques, by covalently linking specific antibodies or by other approaches, like the diabody approach (Kipriyanow, *Int. J. Cancer* 77 (1998), 763-773). In one aspect of the invention, the bispecific antibody is a single chain antibody construct.

For tracking purposes, the bispecific antibody can be directly labeled or a second antibody specific for a region of the bispecific antibody is labeled. Detection of the localization of the chimeric molecule is preferably through cell sorting techniques such as flow cytometry. For example, wherein samples are taken at different time intervals after administration of the chimeric molecule for imaging and diagnostic purposes.

In accordance with the invention, the bispecific antibody, targets chimeric molecules to a specific location in vivo. For example, the location can be to myocardial tissues, breast, liver, spleen, ovaries, testis, hepatocyte, kidneys and the like. The bispecific antibody determines the specific antigen to which the chimeric molecule is targeted.

As described above, the specificity of the antibody domain can be directed to a specific tissue antigen wherein the tumor has been detected coupled with specificity for that particular tumor antigen. Alternatively, the bispecific antibody domain is directed to two tumor antigens that are expressed by the tumor. The bispecific domain can be fused to any FAK-binding molecule domain discussed above.

In another embodiment of the invention, the bispecific antibody (BiAb) construct is a bispecific antibody that binds to one or more tumor antigens as a first or second antigen and a cell or tissue specific antigen a second antigen. The antibody may be covalently bound to the FAK-binding molecule and the chimeric molecule may be constructed by chemical coupling, producing a fusion protein or a mosaic protein from the antibody and from a modified or unmodified prokaryotic or eukaryotic modulatory or cytotoxic molecule. Furthermore, the antibody may be joined to modulatory or cytotoxic molecule via multimerization domains.

In another embodiment of the invention, the chimeric polypeptide of the invention, e.g., a peptide 35 construct, is a fusion construct of a modified or an unmodified FAK-binding molecule with a modified or an unmodified modulatory or cytotoxic molecule. The construct may be bound in vitro and/or in vivo, e.g., by a multimerization domain, to bispecific antibody domain. The chimeric molecule constructs may, inter alia, result from chemical coupling, may be recombinantly produced (as shown in the appended examples), or may be produced as a fusion protein as described above. In one aspect, the moiety specifically binds to at least one tumor antigen.

The compositions of the invention can comprise any cytotoxic agent as described infra. For example, in one aspect, the toxin may be a polypeptide toxin, e.g., a *Pseudomonas* exotoxin, like PE38, PE40 or PE37, or a truncated version thereof, or a ribosome inactivating protein gelonin (e.g., Boyle (1996) *J. Immunol.* 18:221-230), and the like. The compositions of the invention can be conjugated to any cytotoxic pharmaceuticals, e.g., radiolabeled with a cytotoxic agents, such as, e.g., $^{131}$I (e.g., Shen (1997) *Cancer* 80(12 Suppl):2553-2557), copper-67 (e.g., Deshpande (1988) *J. Nucl. Med.* 29:217-225).

In one embodiment, the chimeric molecule construct is a fusion (poly)peptide or a mosaic (poly)peptide. The fusion (poly)peptide may comprise merely the domains of the constructs as described herein, as well as (a) functional fragment(s) thereof. However, it is also envisaged that the fusion (poly)peptide comprises further domains and/or functional stretches. Therefore, the fusion (poly)peptide can comprise at least one further domain, this domain being linked by covalent or non-covalent bonds. The linkage as well as the construction of such constructs, can be based on genetic fusion according to the methods described herein or known in the art (e.g., Sambrook et al., loc. cit., Ausubel, "Current Protocols in Molecular Biology", Green Publishing Associates and Wiley Interscience, N.Y. (1989)) or can be performed by, e.g., chemical cross-linking as described in, e.g., WO 94/04686. The additional domain present in the construct may be linked by a flexible linker, such as a (poly)peptide linker, wherein the (poly)peptide linker can comprises plural, hydrophilic, peptide-bonded amino acids of a length sufficient to span the distance between the C-terminal end of the further domain and the N-terminal end of the peptide, (poly)peptide or antibody or vice versa. The linker may, inter alia, be a Glycine, a Serine and/or a Glycine/Serine linker. Additional linkers comprise oligomerization domains. Oligomerization domains can facilitate the combination of two or several antigens or fragments thereof in one functional molecule. Non-limiting examples of oligomerization domains comprise leucine zippers (like jun-fos, GCN4, E/EBP; Kostelny, *J. Immunol.* 148 (1992), 1547-1553; Zeng, *Proc. Natl. Acad. Sci. USA* 94 (1997), 3673-3678, Williams, *Genes Dev.* 5 (1991), 1553-1563; Suter, "Phage Display of Peptides and Proteins", Chapter 11, (1996), Academic Press), antibody-derived oligomerization domains, like constant domains $C_H1$ and $C_L$ (Mueller, *FEBS Letters* 422 (1998), 259-264) and/or tetramerization domains like $GCN_4$-LI (Zerangue, *Proc. Natl. Acad. Sci. USA* 97 (2000), 3591-3595).

Furthermore, the chimeric fusion construct and/or peptide 35 (SEQ ED NO: 1) to be used in the present invention, as described herein, may comprise at least one further domain, inter alia, domains which provide for purification means, like, e.g. histidine stretches. The further domain(s) may be linked by covalent or non-covalent bonds.

The linkage can be based on genetic fusion according to the methods known in the art and described herein or can be performed by, e.g., chemical cross-linking as described in, e.g., WO 94/04686. The additional domain present in the construct may be linked by a flexible linker, such as a polypeptide linker to one of the binding site domains; the polypeptide linker can comprise plural, hydrophilic or peptide-bonded amino acids of a length sufficient to span the distance between the C-terminal end of one of the domains and the N-terminal end of the other of the domains when the polypeptide assumes a conformation suitable for binding when disposed in aqueous solution.

Nucleic Acids

The invention also provides purified nucleic acids encoding the FAK-binding molecules and the fusion proteins described above. The nucleic acids of the invention may be used to produce peptides or chimeric molecules of the invention, and may be incorporated in a vector. Starting with a known protein sequence, DNA encoding the FAK-binding molecules or the fusion proteins may be prepared by any suitable method, including, for example, cloning and restriction of appropriate sequences or direct chemical synthesis by methods such as the phosphotriester method of Narang et al. (1979) *Meth. Enzymol.* 68: 90-99; the phosphodiester method of Brown et al. (1979) *Meth. Enzymol.* 68: 109-151; the diethylphosphoramidite method of Beaucage et al. (1981) *Tetra. Lett.*, 22: 1859-1862; and the solid support method of U.S. Pat. No. 4,458,066. Due to the degeneracy of the genetic code, a large number of different nucleic acids will encode the FAK-binding molecules and the fusion proteins. Each of these is included within the invention.

Methods of Delivering a FAK-Binding Molecule to a Cell

The invention also provides a method of delivering a FAK-binding molecule to a cell. FAK-binding molecules can be delivered to a cell by any known method. For example, a composition comprising the FAK-binding molecule can be added to cells suspended in medium. Alternatively, a FAK-binding molecules (especially those included in chimeric molecules that contain a membrane permeability domain) can be administered to an animal (e.g., by a parenteral route) to, e.g., target a cell (such as a cancer cell) for induction of apoptosis.

Pharmaceutical Compositions

The FAK-binding molecules (including those conjugated with a second molecule) of this invention can be prepared for parenteral, topical, oral, or local administration, such as by aerosol or transdermally, for prophylactic and/or therapeutic treatment. The pharmaceutical compositions can be administered in a variety of unit dosage forms depending upon the method of administration. The pharmaceutical compositions of this invention are particularly useful for parenteral administration, such as intravenous administration or administration into a body cavity or lumen of an organ. The compositions for administration will commonly comprise a solution of the FAK-binding molecule dissolved in a pharmaceutically acceptable carrier, preferably an aqueous carrier. A variety of aqueous carriers can be used, e.g., buffered saline and the like. These solutions are sterile and generally free of undesirable matter (e.g., pyrogens). These compositions may be sterilized by conventional, well known sterilization techniques. The compositions may comprise pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of FAK-binding molecule in these formulations can vary widely, and will be selected primarily based on fluid volumes, viscosities, body weight and the like in accordance with the particular mode of administration selected and the patient's needs. Actual methods for preparing parenterally administrable compositions will be known or apparent to those skilled in the art and are described in more detail in such publications as *Remington's Pharmaceutical Science,* 15th ed., Mack Publishing Company, Easton, Pa. (1980).

Toxicity and therapeutic efficacy of the pharmaceutical compositions utilized in the invention can be determined by standard pharmaceutical procedures, using either cells in culture or experimental animals to determine the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_5/ED_{50}$. Doses that exhibit large therapeutic indices are preferred. While those that exhibit toxic side effects may be used, care should be taken to design a delivery system that targets the pharmaceutical composition to the site of affected tissue in order to minimize potential damage to uninfected cells and, thereby, reduce side effects.

The data obtained from cell culture assays and animal studies can be used in formulating a range of dosage for use in humans. The dosage of such pharmaceutical compositions lies preferably within a range of circulating concentrations that include an $ED_{50}$ with little or no toxicity. The dosage may vary within this range depending upon the dosage form employed and the route of administration utilized. For any pharmaceutical composition used in a method of the invention, the therapeutically effective dose can be estimated initially from cell culture assays. A dose can be formulated in animal models to achieve an $IC_{50}$ (that is, the concentration of the test compound which achieves a half-maximal inhibition of symptoms) as determined in cell culture. Such information can be used to more accurately determine useful doses in humans. Levels in plasma can be measured, for example, by high performance liquid chromatography. Although dosage should be determined for each particular application, it is expected that a dose of a typical pharmaceutical composition for intravenous administration would be about 0.1 to 10 mg per patient per day. Dosages from about 0.1 up to about 100 mg per patient per day may be used, particularly when the pharmaceutical compositions is administered to a secluded site and not into the blood stream, such as into a body cavity or into a lumen of an organ.

Anti-Cancer and FAK-Binding Molecule Cocktails

The peptide 35 (SEQ ID NO: 1), AV3 (SEQ ID NO: 3) and/or chimeric fusion molecules, including humanized chimeric fusion molecules may also be administered in combination with other anti-cancer agents, e.g., other antibodies or drugs. Also, the subject molecules or fragments may be directly or indirectly attached to effector having therapeutic activity. Suitable effector moieties include by way of example cytokines (IL-2, TNF, interferons, colony stimulating factors, IL-1, etc.), cytotoxins (Pseudomonas exotoxin, ricin, abrin, etc.), radionuclides, such as $^{90}Y$, $^{131}I$, $^{111}In$, $^{125}I$, among others, drugs (methotrexate, daunorubicin, doxorubicin, etc.), immunomodulators, therapeutic enzymes (e.g., beta-galactosidase), anti-proliferative agents, etc. The attachment of antibodies to desired effectors is well known. See, e.g., U.S. Pat. No. 5,435,990 to Cheng et al. Moreover, bifunctional linkers for facilitating such attachment are well known and widely available. Also, chelators (chelants and chelates) providing for attachment of radionuclides are well known and available.

Without further elaboration, it is believed that one skilled in the art can, using the preceding description, utilize the present invention to its fullest extent. The invention will be further clarified by a consideration of the following examples, which are intended to be purely exemplary of the present invention are thus to be construed as merely illustrative examples and not limitations of the scope of the present invention in any way.

EXAMPLES

The present invention is further illustrated by the following specific examples. The examples are provided for illustration only and are not to be construed as limiting the scope or content of the invention in any way.

Materials and Methods

Peptides that bind FAK were isolated by phage display techniques. Baculovirus FAK-CD was the target protein and peptides were isolated from a phage library (New England Biolabs). After three rounds of panning, recovered phages were sequenced to identify potential peptides that bind FAK. Western-blot analysis and phage overlay were used to confirm the binding of these peptides to FAK.

Visualization and penetration of Peptide-35 into breast cancer cells was accomplished by coupling the peptide to FITC and using a TAT penetration sequence. Apoptosis was measured using the Elisa Plus cell death detection assay after cells were treated with drug for 24 hours. Apoptosis was further confirmed by the Hoechst assay.

Cell Culture.

BT474 cells were maintained in RPMI 1640 with 10% fetal bovine serum, 10 μg/ml insulin, and 2 mM L-glutamine. Mouse embryonic fibroblasts were maintained in DMEM with 10% FBS, Amphotericin B, and NEAA. HEK293 human embryonic kidney cells were maintained in DMEM with 10% FBS, and 2 mM L-glutamine. All cells were incubated at 37° C. in 5% $CO_2$.

Plasmids and Transfection.

The mammalian expression vector encoding hemaglutinin (HA)-FAK has been described previously. A 2000 bp region from the 5' end of VEGFR-3 was cloned using TOPO cloning into pcDNA 3.1D/V5-His-TOPO (Invitrogen). Cells were plated at a density of $2 \times 10^6$ cells per 100-mm culture plate and allowed to attach for 24 hours and then transfected by using Effectene (Qiagen) for HEK293 cells according to the manufacturer's protocol.

Reagents and Antibodies.

Peptide-35 and AV3 (SEQ ID NO: 3) were coupled to a TAT sequence (YGRKKRRQRRR; SEQ ID NO: 5) to allow cellular penetration. Peptide-35 was also coupled to FITC for visualization of the peptide inside cells. Anti-FAK, anti-GST, anti-VEGFR-3, and anti-tubulin antibodies were used for immunoprecipitation and western blotting.

Phage Display.

Peptide binding partners to FAK-CD were isolated by phage display. Baculoviral FAK-CD was used as a target and was coated to a plate and peptides were isolated from a phage library containing different 12-amino acids (New England Biolabs). After three rounds of panning, recovered phages were sequenced to identify potential peptides that bind FAK. An isolated peptide (Peptide-35) that bound FAK was found to be homologous to VEGFR-3.

Phage Overlay.

Pure protein (4 μg) with loading buffer was boiled for 10 min and resolved by SDS-PAGE. Proteins were transferred to polyvinylidene difluoride membrane, probed with phage-35, and detected by chemiluminescence (Perkin-Elmer Life Sciences, Inc.).

In Vitro Binding.

GST fusion proteins were purified as previously described. For in vitro binding assay, cell lysates were precleared with GST protein (10 μg), and the cleared supernatants (500 μg) were incubated for 1 hour at 40° C. with 10 μg of GST fusion protein immobilized on glutathione agarose beads. Cell lysates were prepared from BT474 cells. Pure protein (500 ng) was also used to determine binding. The beads were washed three times with cold phosphate buffered saline. The bound proteins were analyzed by Western blotting.

Immunoprecipitation and Western Blotting.

Cell lysates were prepared with 1% NP-40 lysis buffer (20 mM Tris-HCl [pH 7.4], 150 mM NaCl, 1% Nonidet P40, 5 mM EDTA, 1 mM $Na_3VO_4$, 1 mM phenylmethylsulfonyl fluoride, 10 μg of aprotinin/ml, 20 μg of leupeptin/ml). The protein concentration of the lysates was determined by using the Bio-Rad protein assay kit. For immunoprecipitation, 500 μg of total protein were precleared with protein A/G-agarose beads (Calbiochem) at 4° C. for 1 hour and then incubated with 5 μl of antibody overnight followed by a 2 hour incubation with protein A/G-agarose bead at 4° C. Precipitates were washed three times in cold PBS, and beads were resuspended in sodium dodecyl sulfate-polyacrylamide gel electrophoresis (SDS-PAGE) sample loading buffer, boiled for 5 min, and resolved by SDS-PAGE. Proteins were transferred to polyvinylidene difluoride membrane, probed with appropriate antibody, and detected by chemiluminescence (Perkin-Elmer Life Sciences, Inc.).

Immunofluorescence Staining.

Cells were plated onto coverslips in six-well culture plates in medium for 24 hours and stained with anti-FAK and anti-VEGFR-3 antibodies and visualized for co-localization.

Detachment Assay.

Detached and attached cells after drug treatment for 6 hours cells were counted by hemocytometer. The percent detachment was calculated by dividing the number of detached cells by the total number of cells.

Apoptosis Assay.

Cells were treated with drug for 24 hours and then harvested. Hoechst 33342 was added and the specimens were mounted on glass coverslips. The slides were viewed under the microscope for apoptotic nuclei. The percent apoptosis was calculated by dividing the number of apoptotic cells by the total number of cells (300).

Example 1

FAK Binding Peptides

Two potential peptides that bind the C-terminus of FAK were identified using the methods described above. Peptide-32 bound FAK-CD and contained the LD paxillin-binding motif that validated the phage display technique (FIG. 1). Peptide-35 is a twelve amino-acid peptide that binds to specific sequences of FAK-CD (FIG. 2). Peptide-35, coupled to TAT-FITC, was able to penetrate breast cancer cells and cause displacement of FAK from focal adhesions, degradation of FAK, rounding, and detachment in BT474, BT20, and MCF7 breast cancer cells, but not in normal MCF10A cells (FIG. 3). Peptide-35 caused detachment and apoptosis in BT474 breast cancer cells, but not in MCF10A normal breast cells (FIGS. 4 and 5).

Apoptosis has been confirmed in BT474 cells by visualizing nuclear morphology with the Hoechst assay.

Example 2

Characterization of Peptide-Induced Apoptosis in Different Tumor Cell Lines

Preliminary phage display assay revealed peptide 35 (SEQ ID NO: 1) that binds to the C-terminal part of FAK and FAT domain. Peptide-35 caused loss of focal adhesions and apoptosis in cancer cells, but not in normal mammary cancer cell lines, suggesting that it can be a therapeutic drug in cancer cells. BLAST search with peptide-35 detected that this peptide is homologous to a peptide from VEGFR-3 (vascular endothelial growth factor receptor-3) or FLT-4 gene. The synthesized VEGFR-3 (AV-3) peptide caused apoptosis in cancer cells similar to peptide 35. Based on the data, AV-3 peptide (homologous to the twelve amino-acids of VEGFR-3), conjugated with TAT peptide for penetration into cells increased detachment and apoptosis in IMR neuroblastoma cells which express high levels of VEGFR-3. AV-3-induced apoptosis in different cancer cell lines is tested and the structure of peptide-FAK-CD interaction is analyzed.

Example 3

Structural Analysis of FAK-VEGFR-3 Peptide Interaction

Structural analysis of VEGFR-3 peptide binding to the FAT domain of FAK is performed. Structural analysis is by nuclear magnetic resonance (NMR) spectroscopy. The solvent accessible area of the FAT-domain is predominantly hydrophilic with hydrophobic patches located on the helix 1-helix 4 face and the helix 2-helix 3 face. The hydrophobic patches may be involved in paxillin binding interactions. Results from these analyses indicate that NMR approaches will be successful in delineating detailed binding interactions between the inhibitor peptide and the FAT domain.

Preliminary NMR analysis detected binding of VEGFR, AV-3 peptide with chicken FAT, FAK C-terminal domain. The site of peptide binding and is determined and specificity of binding is analyzed. Different scrambled peptides are synthesized to analyze the specificity of NMR assay. Different mutant peptides are synthesized to determine specific amino-acids involved in this interaction.

Example 4

Mapping of FAK and VEGFR-3 Interaction

Peptide 35 (SEQ ID NO: 1) binds C-terminal and FAT domains of FAK, causes apoptosis in cancer cells and is homologous to a peptide from VEGFR-3 or FLT-4 gene. A GST-FLT-4 protein was constructed with 12 amino-acid peptide homologous to 35 peptide inside this GST-fusion protein sequence. GST-FLT-4/VEGFR-3 fusion protein was isolated pull-down assay with FAK-expressing cell lysates was performed. Pull-down assay with GST-VEGFR-3 demonstrated binding with FAK. Thus, the data demonstrated binding of VEGFR-3, receptor mediating angiogenesis and lymphangiogenesis in tumors, plays an important role in metastasis, and is able to bind FAK. VEGFR-3 phosphorylation was inhibited by the Src-specific inhibitor, PP2, connecting VEGFR-3 signaling to the Src kinase pathway. Src binds to FAK and activates FAK. Also, hydrogen peroxide caused VEGFR-3 association with p85 subunit of PI3-kinase, Shc, Grb2, SHP-2 which are binding partners of FAK. The data have also shown that FAK can activate AKT and ERK1/2 in EGFR-over-expressing breast cancer cells that protected these cells from apoptosis. Thus, since FAK is playing a significant role in survival signaling in tumors and interacts with the VEGFR-3-binding proteins, a function of FAK/VEGFR-3 interaction and down-stream signaling in tumor samples will be characterized.

FLT-4 is expressed as two alternatively spliced transcripts 5.8 kb mRNA and 4.5 kb mRNA and encodes two protein isoforms, FLT-4 L (long) and FLT-4S (short) that differ at their C-terminus, with the long form having additional 65 amino acids. C-terminus of long FLT-4 form has additional three tyrosines, Tyr-1333, Tyr-1337, and Tyr-1363, suggesting that the two isoforms may have different signaling functions. The short form of FLT-4 is associated with lymph node metastasis in human breast cancer cells. However, only long form was shown to cause transformation of fibroblasts being able to grow in soft agar. Mutation of tyrosine 1337 in the C-terminus of FLT-long form abrogated transforming capacity of the FLT-4 in fibroblasts. Grb2 and Shc proteins were involved in interaction with FLT-4. The FLT-4 and SHC interaction may be important to FLT-4-mediated transforming activity associated with the long isoform. The differences in the signaling mediated by short and long FLT-4 forms will be defined.

The involvement of the short and long forms of alternatively spliced VEGFR-3 are tested for signaling experiments. The pull-down assay is used. The GST-constructs are used for pull-down analysis with FAK. Lysates of FAK-overexpressing cell lines or purified baculoviral full-length chicken FAK and/or human FAK-CD are used. The pull-down assay is performed by standard technique. Lysates are pre-cleared and baculoviral protein with GST-protein, immobilized on glutathione agarose beads. In brief, the pre-cleared lysates are incubated with the VEGFR-3-GST-fusion protein. After washing steps, lysates are analyzed by Western blot with FAK antibody. The same assay, can be in reverse assay with VEGFR-3 over-expressing lysates and FAK-GST proteins.

Example 5

Regions of FAK and FAK-CD Involved in Interactions with VEGFR-3

We would like to precisely determine what part of FAK binds with VEGFR-3. We hypothesize that VEGFR-3 will bind to C-terminal part of FAK, as our preliminary data suggest that VEGFR-3 binds C-terminal part of FAK. To confirm this binding, N-terminal-GST-FAK, catalytic domain of FAK, C-terminal and FAT-domain GST FAK constructs of FAK are used. The constructs are used in pull-down assay with cell lysates, transfected with VEGFR-3 plasmid or lysate of BT474 cells that have high VEGFR-3 expression.

To determine exact regions of FAK-CD that are involved in interaction with VEGFR-3 different deletion constructs of FAK-CD are used. Deletion mutants of FAK-CD, include but not limited to: del 700-713 (p130, PI3K binding), del 853-891 (GRAF SH3 binding), del 853-1012 (Paxillin binding), del 965-1012 (Talin binding) and Y925F (Grb2 binding) mutant of FAK-CD. 293 cells are transfected with the deletion constructs and these deletion constructs are used for pull-down assays with GST-VEGFR. Thus, the regions of FAK-CD involved in the binding with VEGFR-3 can be determined.

TABLE 1

| Peptide | Cell Line |
|---|---|
| Cell lines Tested | |
| Peptide 35 | Breast Cancer (mcf-7 bt474, bt20) and Normal (mcf10a) |
| VEGFR 3 (AV3 (SEQ ID NO: 3)) | Breast Cancer (bt474), Neuroblastoma (IMR) and Normal (mcf10a) Mouse Fibroblast, FAK/FAK+. Greater detachment in the FAK+ |
| Peptide Sequences | |
| Peptide-35 | 1 2 3 4 5 6 7 8 9 10 11 12<br>W H W Q W T P W S I Q P<br>(SEQ ID NO: 1) |
| 35-SK | 1 2 3 4 5 6 7 8 9 10 11 12<br>H P W Q W T I S W P Q W (K)<br>(SEQ ID NO: 2) |
| AV3 | 1 2 3 4 5 6 7 8 9 10 11 12<br>W H W R P W T P C K M F<br>(SEQ ID NO: 3) |
| AV3-S | 1 2 3 4 5 6 7 8 9 10 11 12<br>M R W T H F W P C P W K<br>(SEQ ID NO: 4) |

OTHER EMBODIMENTS

This description has been by way of example of how the compositions and methods of invention can be made and carried out. Those of ordinary skill in the art will recognize that various details may be modified in arriving at the other detailed embodiments, and that many of these embodiments will come within the scope of the invention.

Therefore, to apprise the public of the scope of the invention and the embodiments covered by the invention, the following claims are made.

All publications and patent documents cited in this application are incorporated in pertinent part, by reference for all purposes to the same extent as if each individual publication or patent document were so individually denoted. By their citation of various references in this document, Applicants do not admit any particular reference is "prior art" to their invention.

What is claimed is:

1. An isolated peptide that specifically binds focal adhesion kinase and induces apoptosis in a cell that expresses focal adhesion kinase; wherein said peptide consists of the amino acid sequence of SEQ ID NO: 3.

2. A chimeric molecule that comprises the peptide of claim 1 and a membrane permeabilization domain.

3. A composition comprising the chimeric molecule of claim 2.

4. A composition comprising a chimeric molecule, wherein the chimeric molecule comprises the peptide of claim 1, and a targeting domain.

5. A composition comprising a chimeric molecule comprising a targeting domain and the peptide of claim 1 or a variant thereof, wherein said variant is at least 90% identical to SEQ ID NO: 3, wherein the chimeric molecule binds focal adhesion kinase.

6. The composition of claim 5, wherein the targeting domain is a membrane permeabilization domain.

7. The composition of claim 6, wherein the membrane permeabilization domain is an HIV TAT domain.

8. The composition of claim 5, wherein the targeting domain is an antibody that binds a tumor antigen.

9. The composition of claim 8, wherein the tumor antigen is selected from the group consisting of HER-2/neu; intestinal carboxyl esterase; alpha-fetoprotein; M-CSF; MUC1; p53; PRAME; PSMA; RAGE-1; RU2AS; survivin; Telomerase; WT1; and CA125.

10. A composition comprising an isolated peptide consisting of the amino acid sequence of SEQ ID NO: 3, or a variant thereof, wherein said variant is at least 90% identical to SEQ ID NO: 3, wherein the peptide or variant binds focal adhesion kinase (FAK), induces cellular apoptosis and inhibits cell motility.

11. The composition of claim 10, wherein the composition is administered to a cell.

12. The composition of claim 10, wherein the peptide or variant induces apoptosis in a tumor.

13. The composition of claim 10, wherein the peptide or variant inhibits cell motility.

14. A composition comprising an isolated peptide consisting of the amino acid sequence of SEQ ID NO: 3.

* * * * *